United States Patent
Gilbert et al.

(10) Patent No.: US 7,601,702 B2
(45) Date of Patent: Oct. 13, 2009

(54) DUTPASE INHIBITORS

(75) Inventors: Ian Gilbert, Dundee (GB); Corinne Nguyen, Cardiff (GB); Gian Filippo Ruda, Dundee (GB); Alessandro Schipani, Dundee (GB); Ganasan Kasinathan, Cardiff (GB); Nils-Gunnar Johansson, Enhörna (SE); Dolores Gonzalez Pacanowska, Granada (ES)

(73) Assignee: Medivir AB, Huddinge (SE)

( * ) Notice: Subject to any disclaimer, the term of this patent is extended or adjusted under 35 U.S.C. 154(b) by 484 days.

(21) Appl. No.: 10/585,281

(22) PCT Filed: Jan. 6, 2005

(86) PCT No.: PCT/GB2005/050001

§ 371 (c)(1), (2), (4) Date: Oct. 2, 2006

(87) PCT Pub. No.: WO2005/066160

PCT Pub. Date: Jul. 21, 2005

(65) Prior Publication Data

US 2008/0300216 A1    Dec. 4, 2008

(30) Foreign Application Priority Data

Jan. 8, 2004 (GB) .................. 0400290.3

(51) Int. Cl.
*A01N 43/04* (2006.01)
*A61K 31/70* (2006.01)

(52) U.S. Cl. .......... 514/50; 514/49; 536/28.1; 536/28.2; 536/28.5; 536/28.51; 536/28.52; 536/28.53; 536/28.54; 536/28.55

(58) Field of Classification Search .......... None
See application file for complete search history.

(56) References Cited

U.S. PATENT DOCUMENTS

| | | | |
|---|---|---|---|
| 5,410,033 A | 4/1995 | Clive et al. | |
| 5,559,101 A | 9/1996 | Weis et al. | |
| 6,627,400 B1 | 9/2003 | Singh | |

FOREIGN PATENT DOCUMENTS

| | | |
|---|---|---|
| JP | 04 054193 | 2/1992 |
| JP | 04 054193 A | 2/1992 |
| JP | 04 077485 A | 3/1992 |
| JP | 04 077485 | 11/1992 |
| JP | 05 247082 | 9/1993 |
| JP | 05 247082 A | 9/1993 |
| JP | 06 065235 | 4/1994 |
| WO | WO 93/02044 | 2/1993 |
| WO | WO 95/07287 | 3/1995 |
| WO | WO 95/07287 A | 3/1995 |
| WO | WO 97/37691 | 10/1997 |
| WO | WO 97/37691 A | 10/1997 |

OTHER PUBLICATIONS

Hidalgo-Zarco, et al., Protein Science, vol. 10(7), (2001), pp. 1426-1433.
Cano, et al., Life Sciences, vol. 61(1), (1997), pp. PL1-8.
O'Dell, et al., Nucleosides Nucleotides, vol. 13(9), (1994), pp. 1929-1937.
Niihata, et al., Bull Chem Soc Japan, vol. 68(8), (1995), pp. 2327-2329.
Takamatsu, et al., Nucleosides Nucleotides Nucleic Acids, vol. 21(11 &12), (2002), pp. 849-861.
Horwitz, et al., J Org Chem, vol. 31(1), (1996), pp. 205-211.
Van Aerschot, et al., Bull Soc Chim Belg, vol. 98(12), (1989), pp. 937-941.
Beach, et al., J Org Chem, vol. 57(14), (1992), pp. 3887-3894.
Von Janta Lipinski, et al., J Med Chem, vol. 41(12), (1998), pp. 2040-2046.
Batoux, et al., Tetrahedron Lett, vol. 42(8), (2001), pp. 1491-1493.
Sukeda, et al., J Org Chem, vol. 65(26), (2000), pp. 8988-8896.
Hidalgo-Zarco, Fernando et al., "Kinetic properties and inhibition of the dimeric dUTPase-dUDPase from Leishmania major," Protein Science, 10(7), 2001, ISSN: 0961-8368, pp. 1426-1433. XP008047778.

(Continued)

*Primary Examiner*—Patrick T Lewis
(74) *Attorney, Agent, or Firm*—Birch, Stewart, Kolasch & Birch LLP

(57) ABSTRACT

Deoxyuridine derivatives of Formula (I'); where A is O, S or $CH_2$; B is O, S or $CHR^3$; $R^1$ is H, or various substituents; $R^2$ is H, F; $R^3$ is H, F, OH, $NH_2$; or $R^2$ and $R^3$ together form a chemical bond; D is —NHCO—, —CONH—, —O—, —C(=O)—, —CH=CH, —C≡C—, —$NR^5$—; $R^4$ is hydrogen or various substituents; $R^5$ is H, $C_1$-$C_4$ alkyl, $C_1$-$C_4$ alkanoyl; E is Si or C; $R^6$, $R^7$ and $R^8$ are independently selected from $C_1$-$C_8$ alkyl, $C_2$-$C_8$ alkenyl, $C_2$-$C_8$ alkynyl, or a stable monocyclic, bicyclic or tricyclic ring system have utility in the prophylaxis of treatment of parasitic diseases such as malaria.

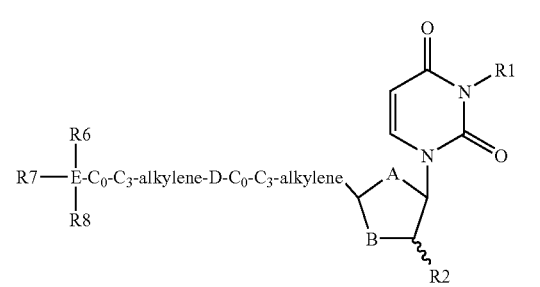

22 Claims, No Drawings

OTHER PUBLICATIONS

Cano, V. et al., "Monometoxytrityl derivatives of uridine as inhibitors . . . ," Life Sciences, 61(1), 1997, ISSN: 0024-3205. XP008047794.

O'Dell, C. Allen et al., "Carbocylic analogs of 3',4'-didehydro-2'deoxyribofuranosyl-2,4(1H,3H)-pyrimidinediones," Nucleosides & Nucleotides, 13(9) 1929-37., Abstract. XP008047788.

Nihata, Shigeo et al, "Synthesis of 2',3'-didehydro-2',3'-dideoxy nucleosides from 2',2'-bis(phenylthio) nucleoside analogs," Bulletin of the Chemical Society of Japan, 68(8), 2327-9. ISSN: 00089-2373, 1995, Abstract. XP008047806.

Takamatsu, Staoshi et al., "Convenient synthesis of fluorinated nucleosides with . . . ," Nucleosides, Nucleotides, & Nucleic Acids, 21(11&12), 2002, 849-861. ISSN: 1525-7770. XP008047806.

Horwitz, Jerome P. et al, "Nucleosides. IX. The formation of . . . ," Journal of Organic Chemistry, 31(1), 1966, 205-11. ISSN: 0022-3263. XP008047787.

Van, Aerschot A. et al., "2,3'-difluoro-and . . . ," Bull. Soc. Chim. Belf., vol. 98, No. 12, 1989, pp. 937-941. XP008047840.

Patent Abstracts of Japan, vol. 016, No. 289 (C-0956), Jun. 26, 1992.

Beach, J.W. et al., "A highly stereoselective synthesis anti-HIV. . . ," Journal of Organic Chemistry, American Journal Society. Easton, US, vol. 57, No. 14, 1992, pp. 3887-3894, ISSN: 0022-3263. XP002953555.

Von Janta-Lipinski, M et al.. "Newly synthesized L-enantiomers of . . . ," Journal of Medicinal Chemistry. Jun. 4, 1998, vol. 41, No. 12, pp. 2040-2046. XP002330488.

Patent Abstracts of Japan. vol. 018, No. 004, Jan. 6, 1994.

Patent Abstracts of Japan, vol. 16., No. 249, Jun. 8, 1992.

US 2001/0020026 A1, 09/2001, Belleau (withdrawn)

DUTPASE INHIBITORS

This application is a national phase under 35 U.S.C § 371 of PCT International Application No. PCT/GB2005/050001 which has an International filing date of Jan. 6, 2005, which designated the United States of America. In addition, this application claims priority to Application No.: 0400290.3 filed in Great Britain, which was filed on Jan. 8, 2004.

FIELD OF THE INVENTION

The present invention relates to pharmaceuticals active against parasite dUTPase and methods for treating parasitical infections, especially malaria, by administering such compounds.

TECHNICAL BACKGROUND

Deoxyuridine triphosphate nucleotidohydrolase (dUTPase) E.C. 3.6.1.23 is an ubiquitous enzyme which hydrolyzes deoxyuridine triphosphate (dUTP) to deoxyuridine monophosphate (dUMP) and pyrophosphate, typically in the presence of magnesium ions. This reaction is thought to occur primarily to limit pools of intracellular dUTP in order to prevent significant uridine incorporation into DNA during replication and repair. A second role of dUTPase is to provide substrate (dUMP) for the de novo synthesis of thymidylate.

Two groups of researchers, McIntosh et al., PNAS, 89:8020-8024 (1992) and Strahler et al., PNAS, 90:4991-4995 (1993), have reportedly isolated the trimeric human dUTPase enzyme and characterized the enzyme by its cDNA and amino acid sequences.

McIntosh reported a cDNA of 526 base pairs containing an ORF which encoded a protein of 141 amino acids and a 3f flanking sequence following the ORF. Strahler reported the identical cDNA and amino acid sequence as did McIntosh, with the exception of two additional bases at the 51 end of the cDNA and a longer 3f flanking sequence. The human dUTPase reported by both groups was found to have a high degree of homology with dUTPase from other organisms including that from yeasts, bacteria and viruses. Strahler further reported that human dUTPase exists in both, phosphorylated and a non-phosphorylated forms.

International patent application no WO97/36916 discloses the sequence of nuclear and mitochondrial isoforms of dUTPase.

In both prokaryotic and eukaryotic cell systems, dUTPase has been clearly shown to be an essential enzyme, without which the cell will die. Lack of dUTPase leads to elevated cellular dUTP pools, resulting in an increased misincorporation of uridine into DNA. In addition to prokaryotes and eukaryotes, a number of viruses, such as herpes simplex, are known to encode a dUTPase function.

International patent application no WO95/15332 proposes a range of uridine di- and triphosphate analogues in which the oxygen atoms between phosphate groups are replaced with methylene, secondary amine or tertiary amine, and/or oxo functions on the phosphate are replaced with sulphur. These compounds are postulated as cytostatics for use against rapidly growing cancer cells and/or antivirals against herpes. Substantially similar compounds are disclosed in Zalud et al Adv. Exp. Med. Biol. 1995 370 135-138 and Persson et al Bioiorg Med Biochem 1996 4 553-556. It should be noted, however that these compounds have been primarily designed for crystallographic purposes and the analysis of enzyme kinetics. These compounds therefore do not possess physico-chemical attributes suggestive of a drug.

The present inventors have established that the substrate specificity of the dUTPases of certain protozoal and bacterial parasites of man differ from the corresponding human cellular and mitochondrial enzymes to such an extent that a specific set of inhibitor compounds can be prepared which selectively inhibit the parasite dUTPase without substantially inhibiting the human counterparts. Examples of such parasites include *Plasmodium* species especially *P. falciparum* responsible for malaria, Mycobacterial species, especially *M. tuberculosum* responsible for tuberculosis and *Leishmania* spp.

Hidalgo-Zarco and Gonzàlez-Pacanowska Current Protein and Peptide Science, 2001, 2, 389-397 describe the isolation and characterisation of trypanosomal dUTPases. In contrast to the trimeric form of dUTPase shared by human and malarial enzymes, the trypanosomal enzyme is a dimmer. Competitive Inhibition of *Leishmania* dUTPase was shown by the triphosphate substrate analogue α-β-imido-dUTP, whereas no inhibition of that parasite was apparent in the case of 5'-O-(4-4'-dimethoxytrityl)-2'-deoxyuridine.

BRIEF DESCRIPTION OF THE INVENTION

In accordance with a first aspect of the invention there are provided use of deoxyuridine derivatives of the formula I, in the manufacture of a medicament for the treatment or prophylaxis of parasitic infections, particularly *plasmodium* infections in mammals, including man.

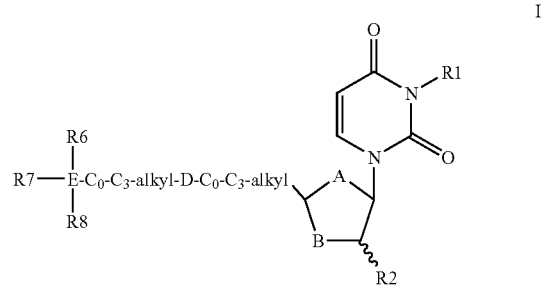

where

A is O, S or $CH_2$;

B is O, S or $CHR^3$;

$R^1$ is H, $C_1$-$C_8$ alkyl, $C_2$-$C_5$ alkenyl, $C_2$-$C_5$ alkynyl or a 5 or 6 membered, saturated or unsaturated ring containing 0 to 3 heteroatoms selected from N, O and S, the alkyl, alkenyl, alkynyl or ring is optionally substituted with $R^4$;

$R^2$ is H or F;

$R^3$ is H, F, OH, $NH_2$ or a pharmaceutically acceptable ester, amide or ether thereof; or $R^2$ and $R^3$ together form a chemical bond;

D is —NHCO—, —CONH—, —O—, —C(=O), —CH=CH, —C≡C—, —$NR^5$—, $R^4$ is independently hydrogen, halo, cyano, amino, nitro, carboxy, carbamoyl, hydroxy, oxo, $C_1$-$C_5$ alkyl, $C_1$-$C_5$ haloalkyl, $C_1$-$C_5$ alkyloxy, $C_1$-$C_5$ alkanoyl, $C_1$-$C_5$ alkanoyloxy, $C_1$-$C_5$ alkylthio, —N($C_0$-$C_3$-alkyl)$_2$, hydroxymethyl, aminomethyl, carboxymethyl; —$SO_2$N($C_0$-$C_3$-alkyl), —$SO_2C_1$-$C_5$-alkyl, where n is 1 or 2;

$R^5$ is H, $C_1$-$C_3$-alkyl, $C_1$-$C_3$-alkanoyl;

E is Si or C;

$R^6$, $R^7$ and $R^8$ are independently selected from $C_1$-$C_8$ alkyl, $C_2$-$C_8$ alkenyl, $C_2$-$C_8$ alkynyl, or a stable monocyclic, bicyclic or tricyclic ring system which is saturated or unsaturated in which each ring has 0 to 3 heteroatoms selected from N, O and S, wherein any the $R^6$, $R^7$ and/or $R^8$ group may be optionally substituted with $R^4$;

and pharmaceutically acceptable salts thereof.

According to a second aspect of the invention there are provided novel compounds of the formula II

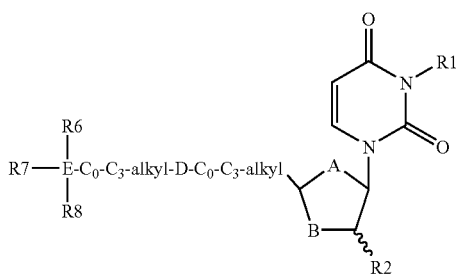

where

A is O, S or $CH_2$;

B is O, S or $CHR^3$;

$R^1$ is H, $C_1$-$C_5$ alkyl, $C_{1-5}$ alkenyl, $C_2$-$C_5$ alkynyl or a 5 or 6 membered, saturated or unsaturated ring containing 0 to 3 heteroatoms selected from N, O and S, the alkyl, alkenyl, alkynyl or ring is optionally substituted with $R^4$;

$R^2$ is H or F;

$R^3$ is H, F, OH, $NH_2$ or a pharmaceutically acceptable ester, amide or ether thereof; or $R^2$ and $R^3$ together form a chemical bond;

D is —NHCO—, —CONH—, —O—, —C(=O)—, —CH=CH, —C≡C—, —$NR^5$—, $R^4$ is independently hydrogen, halo, cyano, amino, nitro, carboxy, carbamoyl, hydroxy, oxo, $C_1$-$C_5$ alkyl, $C_1$-$C_5$ haloalkyl, $C_1$-$C_5$ alkyloxy, $C_1$-$C_8$ alkanoyl, $C_1$-$C_5$ alkanoyloxy, $C_1$-$C_5$ alkylthio, —N($C_0$-$C_3$-alkyl)$_2$, hydroxymethyl, aminomethyl, carboxymethyl; —$SO_nN(C_0$-$C_3$-alkyl), —$SO_nC_{1-5}$ alkyl, where n is 1 or 2;

$R^5$ is H, $C_1$-$C_3$ alkyl, $C_1$-$C_3$ alkanoyl;

E is Si or C;

$R^6$ and $R^7$ are independently selected from a stable monocyclic, bicyclic or tricyclic ring system which has an aromatic nature in which each ring has 0 to 3 heteroatoms selected from N, O and S;

$R^8$ selected from $C_1$-$C_8$ alkyl, $C_2$-$C_8$ alkenyl, $C_2$-$C_8$ alkynyl, or a stable monocyclic, bicyclic or tricyclic ring system which is saturated or unsaturated in which each ring has 0 to 3 heteroatoms selected from N, O and S; wherein $R^6$, $R^7$ and $R^8$ group are optionally substituted with $R^4$;

with the proviso that if the group $C_0$-$C_3$alkyl-D-$C_0$-$C_3$ alkyl is —O—$CH_2$—, then the group E($R^6$)($R^7$)($R^8$) is not trityl, methoxylated trityl or tert.butyldiphenylsilyl;

or a pharmaceutically acceptable salt thereof.

The novel compounds of the invention are useful in methods for the treatment or propylaxis, or in the manufacture of a medicament for such treatment or prophylaxis, of parasitic infections, such as *Leishmania*, trypansoma, human African trypanosomiasis, Chagas disease or *plasmodium* (malaria).

The potency and selectivity of the compounds and methods of the invention, which presuppose substantial lipophilicity at the 5' position is surprising bearing in mind that the active site of the dUTPase enzyme is intended to recognize and accommodate highly polar, hydrophilic moieties, ie the triphosphorylated nucleotides.

Conveniently, A is —O— and B is —$CHR^3$— thus defining a 2'-deoxyribose analogues.

Alternative preferred variants include those where A is —O— and B is —O—, or —S—, thus defining a dioxolane or especially an oxathiolane derivative.

Other preferred variants include those wherein $R^2$ and $R^3$ form a chemical bond and A is —O—, thus defining a 2'3'-dideoxy, didehydroribose derivative or $R^2$ and $R^3$ are H, thus defining a 2',3'-dideoxyribose derivative.

Still further preferred variants include those wherein $R^2$ and $R^3$ form a chemical bond and A is —$CH_2$—, thus defining a 2-cyclopentene derivative or those wherein $R^2$ and $R^3$ are H, thus defining a cyclopentane derivative.

It is currently preferred that $R^3$ is H, $NH_2$, OH or F. An alternative, but currently less favoured, $R^3$ is a lipophilic ester such as straight or branched chain alkyl or benzyl ester or an ether such as straight or branched chain alkyl or benzyl ether or alkylated silyl function.

$R^1$ is preferably a small substituent, most preferably H.

Favoured $C_0$-$C_3$-alkylene-D-$C_0$-$C_3$-alkylene configurations include aminomethylene, aminoethylene and aminopropylene, methylaminomethylene, methylaminoethylene, ethylaminomethylene, —(N-methyl)aminomethylene, —(N-methyl)aminoethylene, —(N-methyl)aminopropylene and methyl-(N-methyl)aminomethylene. Currently the most preferred is -aminomethylene-. The order of the hetero atom and alkylene moieties in the indicated groups as used herein corresponds to the configuration of Figure I or II as depicted above, that is "aminomethylene" has the nitrogen atom adjacent E and the methylene moiety proximal to the base.

Particularly preferred $C_0$-$C_3$-alkylene-D-$C_0$-$C_3$-alkylene configurations include —O—, oxymethylene, oxyethylene, oxypropylene methyloxymethylene and methyloxyethylene. Currently the most preferred in this series is -oxymethylene-.

Preferably at least one of $R^6$, $R^7$ and/or $R^8$ has an aromatic nature, although this tends to be less important if $R^3$ has a lipophilic nature. Conveniently two of $R^6$, $R^7$ and/or $R^8$ have an aromatic nature and the invention even embraces compounds wherein all three have an aromatic nature.

Ring systems for $R^6$, $R^7$ and/or $R^8$ are typically bonded direct to E, but may optionally be bonded to E via a methylene linker. For example $R^6$ may be optionally substituted benzyl, thereby representing phenyl bonded through a methylene to E.

Ring systems for $R^6$, $R^7$ and/or $R^8$ having an aromatic nature include optionally substituted heteroaryls such as furyl, thienyl, pyrrolyl, pyrrazolyl, imidazolyl, pyridyl, pyrimidinyl, pyridazinyl, oxazolyl, isoxazolyl, thizolyl, isothiazolyl, especially pyridyl; and optionally substituted carbocycles such as phenyl. Ring systems having an aromatic nature also include multi-ring systems wherein only one ring has an aromatic nature such as indolinyl and ring systems wherein more than one ring has an aromatic nature such as naphthyl or any of the above heterocyclic rings fused to phenyl, such as benzimidazolyl.

Convenient values for $R^6$, $R^7$ and/or $R^8$ include heterocycles such as furyl, thienyl, pyranyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, especially pyridyl, and carbocycles such as cycloalkyl, cycloalkenyl and especially phenyl. Alternative values for $R^6$, $R^7$ and/or $R^8$ include straight or branched alkyl, including methyl, ethyl, i-propyl and t-butyl.

The optional substituent(s) to $R^6$, $R^7$, and/or $R^8$ include 1 to 3, preferably 1 substituent per ring, selected from halo, preferably fluoro, cyano (preferably cyano), amino, nitro, carboxy, carbamoyl, hydroxy, oxo, $C_1$-$C_5$ alkyl, preferably methyl or t-butyl, $C_1$-$C_5$ haloalkyl, preferably trifluoromethyl, $C_1$-$C_5$ alkyloxy, preferably methoxy, $C_1$-$C_5$ alkanoyl, preferably acetyl, $C_1$-$C_5$ alkanoyloxy, preferably acetoxy, $C_{1-5}$ alkylthio, —N($C_0$-$C_3$-alkyl)$_2$, preferably NHMe or NMe, hydroxymethyl, aminomethyl, carboxymethyl; —SO$_n$N($C_0$-$C_3$-alkyl) (n=1, 2), preferably SO$_2$NH$_2$ or SO$_2$NMe or —SO$_n$$C_1$-$C_5$-alkyl, (n=1, 2) preferably sulphonylmethyl or sulphinylmethyl.

Favoured $R^6(R^7)(R^8)$-E-configurations include —C(Ph)$_3$ (trityl), —CH(Ph)$_2$, —CH$_2$Ph, —Si(Ph)$_2$(t-Bu), 1,1-bis(4-methylphenyl)-1'-pyrenylmethyl, where Ph is phenyl or phenyl substituted with $R^4$.

Note, however, that the novel compounds of the invention exclude by way of proviso certain compounds with common protecting groups at the 5'-oxygen of the nucleoside, such as 5'-O-trityl, methoxylated 5'-O-trityl or 5'-O-tert.butyldiphenylsilyl. Accordingly 5'-O-(4',4'-dimethoxytrityl)-2'-deoxyuridine is outside the scope of the novel compound aspect of the invention. This exclusion of trityl and tBuPh$_2$Si in the compound claims only is not believed to be required in respect of other permutations of $C_0$-$C_3$alkyl-D-$C_0$-$C_3$ alkyl, such as compounds wherein D is N. The novel compounds of the invention will however typically avoid conventional hydroxyl protecting groups (such as those cited in Greene below), when $C_0$-$C_3$alkyl-D-$C_0$-$C_3$ alkyl is —O—CH$_2$—. It will be appreciated, however, that the use/method of treatment aspects of the invention include those compounds excluded from the compound claims by proviso.

Compounds wherein E is carbon are currently favoured on pharmacokinetic grounds, although compounds with E as Si have shown advantageous potency and selectivity.

The compounds of the invention include a number of chiral centres, and the invention extends to include racemates, enantiomers and stereoisomers at each of these centres. For example the ring carbon attached to the uracil N1 in Formula I may be in the alpha (down) or preferably the beta (up) configuration. $R_2$ as F in Formula I may be in the ribo (down) position although it is currently preferred to have the arabino (up) position. It is currently preferred that the ring carbon intermediate A and B in Formula I projects the adjacent $C_0$-$C_3$ alkylene in the beta configuration.

Compounds of the invention are generally at least 80% preferably at least 90% such as 97% stereoisometrically pure at chiral centres.

Additional aspects of the invention include a pharmaceutical composition comprising a compound of the formula I in conjunction with a pharmaceutically acceptable carrier or diluent therefore. The invention further provides a method for the treatment or prophylaxis of parasite infections, such as malaria, tuberculosis or leishmaniasis, in man or a zoonose vector comprising the administration of an effective amount of a compound of the formula I to a patient in need thereof, or to the vector.

While it is possible for the active agent to be administered alone, it is preferable to present it as part of a pharmaceutical formulation. Such a formulation will comprise the above defined active agent together with one or more acceptable carriers or excipients and optionally other therapeutic ingredients. The carrier(s) must be acceptable in the sense of being compatible with the other ingredients of the formulation and not deleterious to the recipient.

The formulations include those suitable for rectal, nasal, topical (including buccal and sublingual), vaginal or parenteral (including subcutaneous, intramuscular, intravenous and intradermal) administration, but preferably the formulation is an orally administered formulation. The formulations may conveniently be presented in unit dosage form, e.g. tablets and sustained release capsules, and may be prepared by any methods well known in the art of pharmacy.

Such methods include the step of bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of Formula I or its pharmaceutically acceptable salt in conjunction or association with a pharmaceutically acceptable carrier or vehicle. If the manufacture of pharmaceutical formulations involves intimate mixing of pharmaceutical excipients and the active ingredient in salt form, then it is often preferred to use excipients which are non-basic in nature, i.e. either acidic or neutral.

Formulations for oral administration in the present invention may be presented as discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion and as a bolus etc.

With regard to compositions for oral administration (e.g. tablets and capsules), the term suitable carrier includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethyl cellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, stearic acid, glycerol stearate, silicone fluid, talc waxes, oils and colloidal silica. Flavouring agents such as peppermint, oil of wintergreen, cherry flavouring or the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier. Dosages are set in the conventional manner to take into account the severity of the disease, the susceptibility of the parasite strain, the size and metabolic health of the patient, the mode and form of administration, concomitant medication and other relevant factors. The compounds of the invention may be administered at a daily dose generally in the range 0.1 to 200 mg/kg/day, advantageously, 0.5 to 100 mg/kg/day, more preferably 10 to 50 mg/kg/day, such as 10 to 25 mg/kg/day. A typical dosage rate for a normal adult will be around 50 to 500 mg, for example 300 mg, once or twice per day.

The compounds of formula I can form salts which form an additional aspect of the invention. Appropriate pharmaceutically acceptable salts of the compounds of formula I include salts of organic acids, especially carboxylic acids, including but not limited to acetate, trifluoroacetate, lactate, gluconate, citrate, tartrate, maleate, malate, pantothenate, isethionate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-napthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

Examples of monocyclic rings for $R^1$ include heterocycles such as furyl, thienyl, pyranyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, especially pyridyl, and carbocycles such as cycloalkyl, cycloalkenyl and phenyl.

Examples of monocyclic, bicyclic or tricyclic rings for $R^6$, $R^7$ and/or $R^8$ include heterocycles such as furyl, thienyl, pyranyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, thiadiazolyl, tetrazolyl, triazolyl, and the like or bicyclic rings especially of the above fused to a phenyl ring such as indolyl, quinolyl quinolinyl, isoquinolinyl, benzimidazolyl, benzothiazolyl, benzoxazolyl, benzotriazolyl, benzofuryl, benzothienyl etc. Additional rings include xanthenyl (such as 9-xanthenyl, 9-alkylxanthenyl, 9-phenylxanthenyl, 9-(9-phenyl)xanthenyl, 9-heteroarylxanthenyl, 9-(9-heteroaryl)xanthenyl), dibenzosuberyl, 5-dibenzosuberyl, fluorenyl (such as 5-fluorenyl, 5-(5-alkyl)fluorenyl, 55-heteroaryl)fluorenyl) and the like.

Examples of monocyclic, bicyclic or tricyclic ring systems with an aromatic nature for $R^6$, and/or $R^7$ include heteroaryls such as furyl, thienyl, pyrrolyl, pyrazolyl, imidazolyl, pyridyl, pyrazinyl, pyrimidinyl, pyridazinyl, oxazolyl, isoxazolyl, thiazolyl, isothiazolyl, thiadiazolyl, tetrazolyl, triazolyl, and the like or bicyclic rings especially of the above fused to a phenyl ring such as indolyl, quinolyl, quinolinyl, isoquinolinyl, benzimidazolyl, benzothiazolyl, benzoxazolyl, benzotriazolyl, benzofuryl, benzothienyl etc. Additional rings include xanthenyl (such as 9-xanthenyl, 9-alkylxanthenyl, 9-(9-alkyl)xanthenyl, 9-phenylxanthenyl, 9-(phenyl)xanthenyl, 9-heteroarylxanthenyl, 9-(9-heteroaryl)xanthenyl), dibenzosuberyl, 5-dibenzosuberyl, fluorenyl (such as 5-fluorenyl, 5-(5-alkyl)fluorenyl, 5-(5-phenyl)fluorenyl, 5-(5-heteroaryl)fluorenyl) and the like.

Examples of carbocycles for $R^6$, $R^7$ and/or $R^8$ include monocyclic rings such as phenyl, cyclohexenyl, cyclopentenyl, cyclohexanyl, cyclopentanyl, bicyclic rings such as indanyl, napthyl, and tricyclic rings such as adamantyl, and the like.

The carbo or heterocyclic ring may be bonded via a carbon or via a hetero atom, typically a nitrogen atom, such as N-piperidyl, N-morpholinyl etc. Other examples of such ring systems may also be found in J. Fletcher, O. Dermer, R. Fox, Nomenclature of Organic Compounds, pp. 20-63 (1974).

The term "$C_1$-$C_5$ alkyl" includes such groups as methyl, ethyl, n-propyl, isopropyl, n-butyl, s-butyl, t-butyl, cyclopropyl, n-pentyl and the like with $C_1$-$C_8$ alkyl further including n-hexyl, 3-methylpentyl, and the like.

The term "halo" and "halogen" refer to chloro, bromo, iodo, and especially fluoro.

"$C_1$-$C_5$ alkoxy" refers to those groups such as methoxy, ethoxy, propoxy, t-butoxy and the like.

"$C_2$-$C_5$ alkenyl" refers to those groups such as vinyl, 1-propen-2-yl, 1-butene-4-yl, 1-pentene-5-yl, 1-butene-1-yl and the like, with $C_2$-$C_8$ alkenyl further including hex-3-enyl and the like.

"$C_1$-$C_5$ alkylthio" refers to those groups such as methylthio, ethylthio, t-butylthio, and the like.

"$C_1$-$C_5$ alkanoyl" refers to groups such as acetyl, propionyl, butyryl and the like.

"$C_1$-$C_5$ alkanoyloxy" refers to those groups such as acetoxy, propionoxy, formyloxy, butyryloxy, and the like.

The term "$C_2$-$C_8$ alkenoxy" includes groups such as ethenyloxy, propenyloxy, iso-butoxy ethenyl, and the like.

The term "$C_2$-$C_5$ alkynyl" includes groups such as ethynyl, propynyl, butynyl, pentynyl, and the like with $C_2$-$C_8$ alkynl further including hexynyl and the like.

The term "halo $C_1$-$C_5$ alkyl" includes alkyls substituted 1, 2 or 3 times by a halogen including groups such as trifluoromethyl, fluoromethyl, 2-dichloroethyl, 2,2-difluoroethyl, 2,2,2-trifluoroethyl, 3,3-difluoropropyl, 1,1-2,2,2 pentafluoroethyl and the like.

The term —$C_0$-$C_3$-alkylene- as a bivalent in expressions such as —$C_0$-$C_3$-alkylene-D-$C_0$-$C_3$-alkylene includes a bond (i.e $C_0$), methylene ($C_1$), ethylene ($C_2$), 1,1-dimethyl-methylene ($C_3$), propylene ($C_3$) and the like, with each —$C_0$-$C_3$-alkylene- being selected independently.

The term ($C_0$-$C_3$-alkyl) in monovalent expressions includes H (i.e $C_0$), Me ($C_1$), Et ($C_2$), propyl (C3) with each $C_0$-$C_3$-alkyl being selected independently. Accordingly —N(C alkyl)$_2$ includes —NH$_2$, —NHMe, NHEt NHPr, —N(Me)$_2$, N(Et)$_2$ etc, —SO$_2$N($C_0$-$C_3$-alkyl)$_2$, includes —SO$_2$NH$_2$, —SO$_2$NHMe, —SO$_2$N(Me)$_2$ etc.

As used herein, "the esters, amides and ethers thereof" refer to the appropriate derivatives of each of the preceding hydroxyl or amino groups in the respective definition.

Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); amino acid esters (for example, L-valyl or L-isoleucyl); and mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises an optionally $R^4$-substituted phenyl group.

Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like.

Alternative aryl or heteroaryl esters include benzoyl, pyridylmethyloyl and the like any of which may be substituted with $R^4$. Preferred pharmaceutically acceptable esters include aliphatic L-amino acid esters such as leucyl, isoleucyl and especially valyl. Additional preferred amino acid esters include the 2-O-AA-$C_3$-$C_{22}$ fatty acid esters described in WO99 09031, where AA is an aliphatic amino acid ester, especially those derived from L-lactic acid and L-valyl.

Pharmaceutically acceptable ethers include straight or branched chain saturated or omega 6 unsaturated $C_1$-$C_{22}$ alkyl ethers such as methyl ethers, t-butyl ethers or aryl or heteroaryl ethers such as phenoxy, benzylether, pyridylmethyl ether, any of which may be substituted with $R^4$.

Alternative ethers include alkylated silyl functions such as —Si($C_1$-$C_5$-alkyl)$_3$ such as —Si(t-Bu)(CH$_3$)$_2$, or —Si(Ph)$_2$(t-Bu), —C(Ph)$_3$(trityl), —CH(Ph)$_2$, —CH$_2$Ph, 1,1-bis(4-methylphenyl)-1'-pyrenylmethyl and the like.

Pharmaceutically acceptable amides include those derived from $C_1$-$C_{22}$ branched or straight chain aminoalkyl optionally including 1 to 3 unsaturations and/or optionally substituted with $R^4$, or anilines or benzylamines. Preferred amides include those formed from reaction of the amine with a $C_1$-$C_4$ straight or branched chain alkanoic acid. Other pharmaceutically acceptable amides of amine functions of $R^2$ or $R^{11}$ correspond to the esters indicated above.

It is currently preferred that the ester, amide or ether is lipophilic in nature.

Compounds of the invention are typically synthesized as outlined below.

Scheme 1 depicts a method for alkylation of the 5'-position of a nucleoside or a nucleoside analogue.

Scheme 1

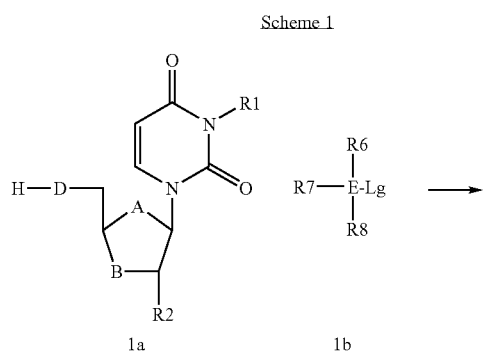

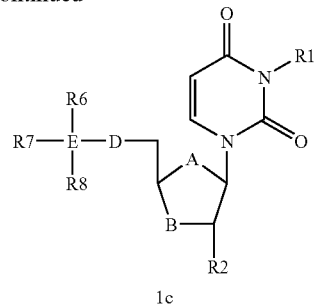

1c

Nucleoside derivative (1a) wherein A, B, $R^1$ and $R^2$ are as defined above for formula I and D is O or NH, can be reacted with an alkylating agent of formula 1b wherein $R^6$, $R^7$, $R^8$ and E are as defined above for formula I and Lg is a leaving group that can be replaced by the nucleophile D, in a solvent like pyridine optionally in the presence of a catalyst such as dimethylaminopyridine or in a solvent like dimethylformamide in the presence of a catalyst like imidazole, to provide 5'-alkylated nucleoside analogues (1c). Various alkylating agents (1b) are available either commercially or in the literature, se for example Greene, "Protective Groups in Organic Synthesis (John Wiley & Sons, New York, 1981). For example, they can be prepared by transforming the hydroxy group of the corresponding alcohol into a leaving group such as a halide like chloride or bromide by treatment with a halogenating agent such as acetyl bromide or thionyl chloride or the like or they can be transformed into a derivative of sulfonic acid like a mesyl, tosyl, triflate or the like by treatment with for example the anhydride or acid chloride of the desired sulfonic acid derivative. An example of a route to alkylating agents is shown in scheme 2.

Scheme 2

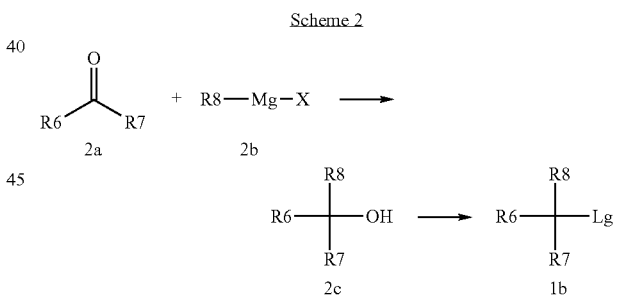

Reaction of an electrophilic carbonyl compound like a keto compound (2a) or any carboxylic acid derivative for instance an ester or acid halide, and a suitable nucleophile for example a Grignard reagent (2b) or an organolithium reagent, provides the alcohol (2c). The formed hydroxy group can subsequently be transformed into a leaving group as described above thus forming the alkylating agent (1b). Examples of the above procedure are described in the literature, se for example Hodges et al., J. Org. Chem. 56, 1991, 449-452, and Jones et al., J. Med. Chem. 33, 1990, 416-419.

Compounds wherein the leaving group in the alkylating agent (1b) is spaced by a $C_1$-$C_3$ alkylene chain, available either commercially or in the literature, may also be used as alkylating agents in scheme 1. An example of a route to a compound containing a $C_2$-alkylene chain is shown in scheme 3.

Scheme 3

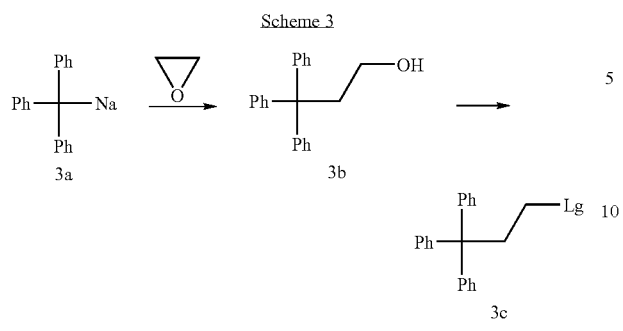

A reaction performed with triphenylmethyl sodium (3a) and ethylene oxide provides alcohol (3b). Subsequent transformation of the hydroxy group into a leaving group for example as described above provides alkylating agent (3c). Use of any other appropriate electrophilic reagent for example formaldehyde, provides analogues with other length of the $C_1$-$C_3$-alkyl chain. Se for example Wooster et al., J. Amer. Chem. Soc., 60, 1938, 1666 and McPhee et al., J. Amer. Chem. Soc. 65, 1943, 2177, 2180. Alternatively, alkylating agents containing a $C_1$-$C_3$-alkyl chain may be obtained by reduction of an appropriate acyl derivative to the desired alcohol.

A suitable acylating agent like the acid chloride or anhydride can be used to acylate the amino group of a 5'-aminonucleoside, thus providing compounds according to the general formula I where D is —CONH—.

The 5'-substituent can also be introduced by way of a Mitsunobu reaction of a desired alcohol and the 5'-unprotected nucleoside derivative as illustrated in scheme 3A.

Scheme 3A

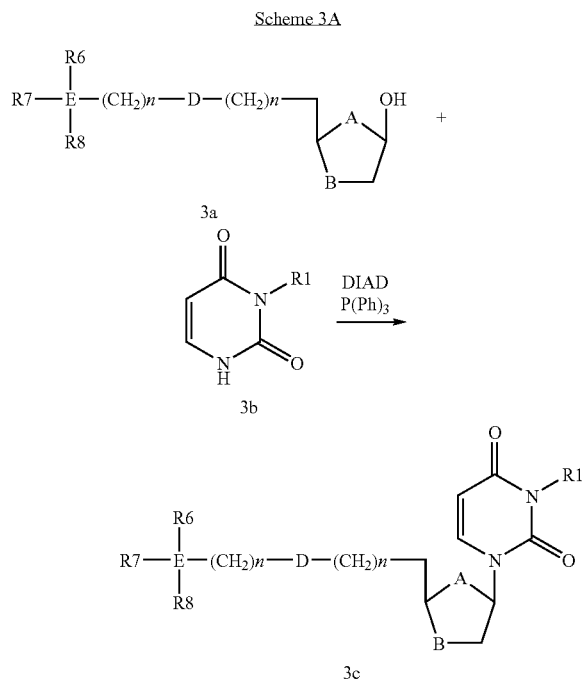

n is 0, 1, 2, 3

Treatment of a desired optionally suitably protected alcohol (3Aa) and a nucleoside derivative (3Ab) with triphenyl phosphine and DIAD in a solvent like THF provides the nucleoside analogue (3Ac).

An example of the introduction of an ether group at the 3-position of the nucleoside analogue is shown in scheme 4.

Scheme 4

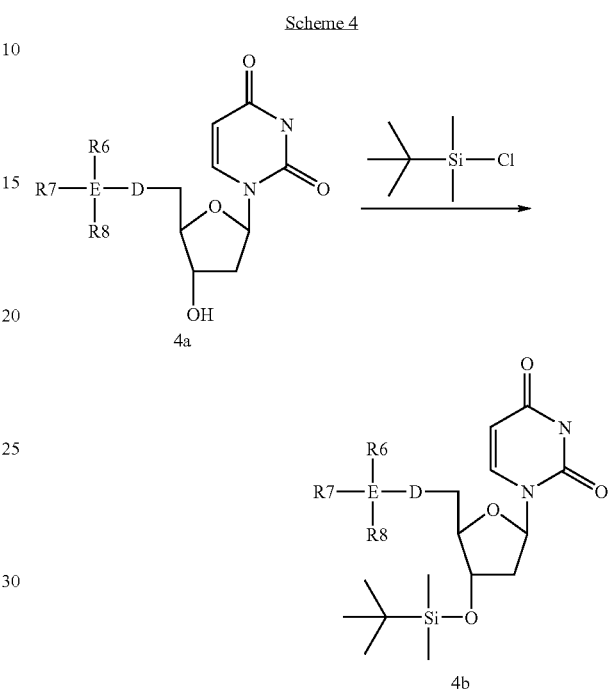

Treatment of a 5'-substituted nucleoside analogue (4a) with a silylating agent for example tert-butyldimethylsilyl chloride in a solvent like dimethylformamide in the presence of a catalyst like imidazole, provides 3'-O-silylated derivatives (4b).

Other ether or ester groups can be introduced at the 3'-position by methods known in the art, for example by treating the 3'-OH nucleoside with the desired alkylating or acylating agent optionally in the presence of a suitable base, se for example Greene, "Protective Groups in Organic Synthesis (John Wiley & Sons, New York, 1981).

Nucleoside analogues used in the synthesis of compounds according to the present invention are available either commercially or in the literature or they can be prepared as described herein. For example compound 1 wherein B is $CH_2F$, $R^1$ and $R^2$ are H and A and D are O i.e. FLU (3'-fluoro-2',3'-dideoxyuridine) can be prepared in analogy with the procedure described for FLT (Balzarini et al. Biochem. Pharmacol. 37, 2847, 1988). The didehydro derivative d4U (2',3'-didehydro-2,3'-dideoxyuridine) can be prepared in analogy with the procedure described for d4T (2',3'-didehydro-2',3'-dideoxythymidine, Stavudine, Balzarini et al.; Mol. Pharmacol. 32, 162, 1987). 2'-Fluoro-2'deoxyarabinofuranosyluracil is conveniently prepared for example as described by H. Howell in J. Org. Chem., 53, 85, 1988 and the corresponding ribo derivative, 2'-fluoro-2'deoxyribofuranosyluracil can be prepared as described for example by Mercer et al. in J. Med. Chem., 30, 670-675, 1987.

5'-aminonucleoside analogues, useful for the preparation of compounds according to the general formula I wherein D is NH or —CONH— can be prepared from the corresponding 5'-alcohols by a displacement-reduction sequence for example as shown in scheme 5.

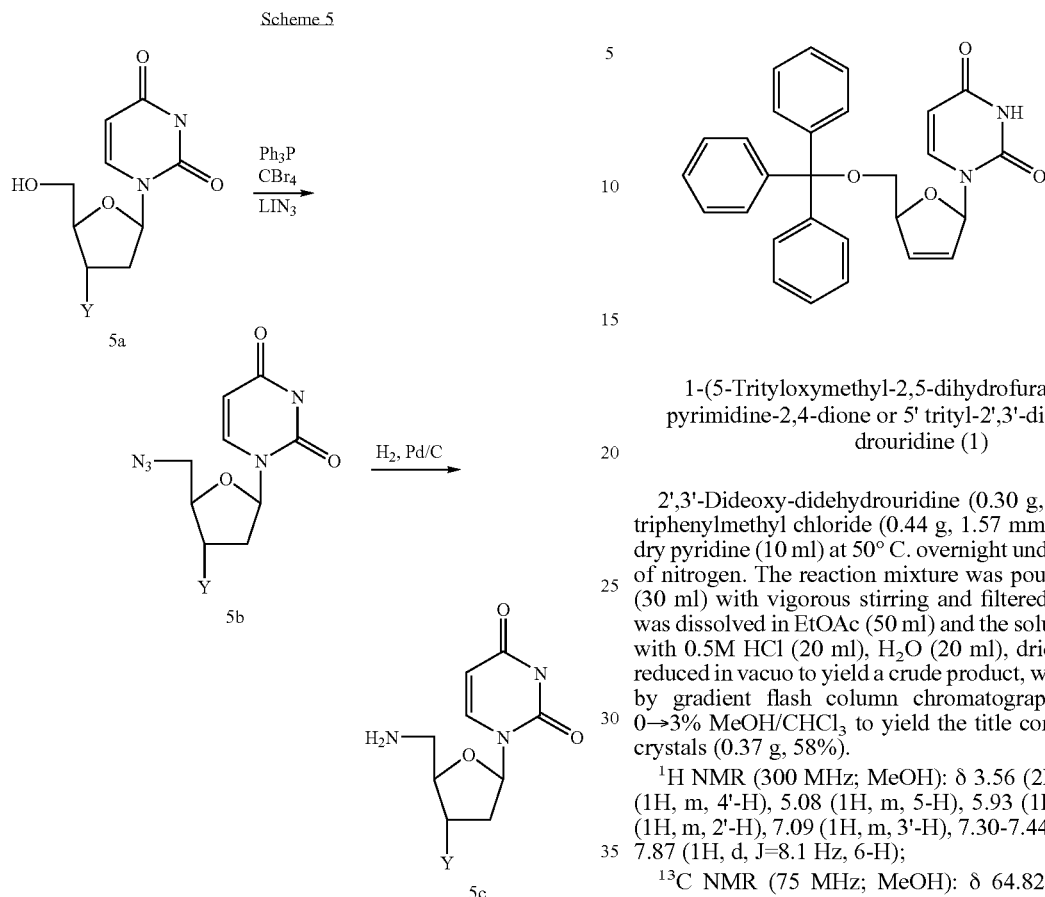

Nucleoside analogue 5a where Y is F or suitably protected OH or NH$_2$, can be reacted with triphenylphosphine in a solvent like carbon tetrabromide followed by displacement of triphenylphosphine oxide with azide ion to form 5b. Alternatively the hydroxy group can be transformed into a leaving group such as a halide like chloride or bromide or a derivative of sulphonic acid such as a tosyl, mesyl or a triflyl group which is subsequently displaced by azide ion. Reduction of the azide group for example by catalytic hydrogenation over palladium on carbon, gives the amino derivative 5c.

The procedures described in scheme 5 can be also applied to carbocyclic uridine and thiouridine analogues providing compounds useful for the preparation of compounds of the general formula I wherein A is CH$_2$ and S.

DETAILED DESCRIPTION OF THE EMBODIMENTS

Various aspects of the invention, including end product inhibitors and intermediates towards those inhibitors will now be described by way of illustration only with reference to the following non-limiting examples. Note that the exemplified intermediates, such as the acyclic side chain building blocks are readily reacted with alternative bases to form additional compounds of the invention.

Example 1

1-(5-Trityloxymethyl-2,5-dihydrofuran-2-yl)-1H-pyrimidine-2,4-dione or 5' trityl-2',3'-dideoxydidehydrouridine (1)

2',3'-Dideoxy-didehydrouridine (0.30 g, 1.43 mmol) and triphenylmethyl chloride (0.44 g, 1.57 mmol) was stirred in dry pyridine (10 ml) at 50° C. overnight under an atmosphere of nitrogen. The reaction mixture was poured into ice-H$_2$O (30 ml) with vigorous stirring and filtered. The precipitate was dissolved in EtOAc (50 ml) and the solution was washed with 0.5M HCl (20 ml), H$_2$O (20 ml), dried (Na$_2$SO$_4$) and reduced in vacuo to yield a crude product, which was purified by gradient flash column chromatography eluting with 0→3% MeOH/CHCl$_3$ to yield the title compound as white crystals (0.37 g, 58%).

$^1$H NMR (300 MHz; MeOH): δ 3.56 (2H, m, 5'-H), 5.02 (1H, m, 4'-H), 5.08 (1H, m, 5-H), 5.93 (1H, m, 1'-H), 6.40 (1H, m, 2'-H), 7.09 (1H, m, 3'-H), 7.30-7.44 (15H, m, Ph-H), 7.87 (1H, d, J=8.1 Hz, 6-H);

$^{13}$C NMR (75 MHz; MeOH): δ 64.82 (5'-CH$_2$), 86.38 (1'-CH), 87.84 (a), 90.04 (4'-CH), 102.70 (5-CH), 126.79 (Ph-CH), 127.79 (2'-CH), 128.41 (Ph-CH), 129.20 (Ph-CH), 134.89 (3'-CH), 141.79 (6-CH), 143.49 (Ph-C), 151.04 (2-C), 159.95 (4-C);

MS (Cl/NH$_3$., m/z); 470.2 (M+NH$_4^+$, 100%), 453.1 (M+H$^+$, 20%);

HRMS (ES+ve., M+H): Calculated for C$_{28}$H$_{24}$N$_2$O$_4$, requires 453.1814; found 453.1807.

IR$_{vmax}$/cm$^{-1}$ (KBr): 714 and 756 (Aromatic, monosubstituted), 1681.0 (C=O) and 1692.3 (C=O); Mp: 68° C., R$_f$ (10% MeOH/CHCl$_3$): 0.30.

Example 2

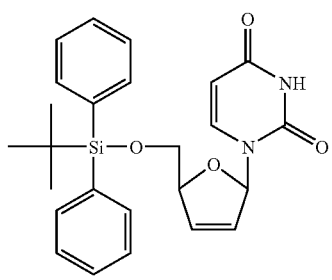

5'-O-tert-butyldiphenylsilyl-2',3'-dideoxydidehydrouridine (2)

2'3'-dideoxy-didehydrouridine (0.30 g, 1.43 mmol) in dry DMF (10 ml) were added drop-wise under an atmosphere of nitrogen, with ice bath cooling, to a stirred solution of tert-butyldiphenylsilylchloride (0.41 ml, 1.57 mmol) and imidazole (0.21 g, 3.14 mmol) in dry DMF (10 ml). The mixture was allowed to warm to room temperature and stirred overnight. H$_2$O (10 ml) was added and the mixture was extracted with CHCl$_3$ (2×30 ml). The combined extracts were washed with saturated aqueous NaHCO$_3$ solution (10 ml) and H$_2$O (10 ml), dried (Na$_2$SO$_4$) and reduced in vacuo to obtain a crude product, which was purified by gradient flash column chromatography eluting with 0→3% MeOH/CHCl$_3$ to yield the title compound as colourless viscous oil (0.46 g, 73%).

$^1$H NMR (300 MHz; MeOH): δ 1.15 [9H, s, C(CH$_3$)$_3$], 3.95 (1H, dd, J=2.9, 11.7 Hz, 5'-H), 4.06 (1H, dd, J=2.9, 11.7 Hz, 5'-H), 4.97 (1H, m, 4'-H), 5.26 (1H, d, J=8.1 Hz, 6-H), 5.58 (1H, m, 1'-H), 6.38 (1H, m, 2'-H), 7.10 (1H, m, 3'-H), 7.34-7.55 (6H, m, Ph-CH), 7.66-7.81 (5H, m, Ph-H and 6-H).

$^{13}$C NMR (75 MHz; MeOH): δ 19.81 [C(CH$_3$)$_3$], 26.99 and 27.42 [C(CH$_3$)$_3$ ], 65.40 (5'-CH$_2$), 87.56 (1'-CH), 90.06 (4'-CH), 102.96 (5-CH), 126.96 (2'-CH), 128.41 (Ph-CH), 128.32 (Ph-CH), 128.12 (Ph-CH), 130.03 (Ph-CH), 130.47 (Ph-CH), 130.59 (Ph-CH), 132.78 (Ph-C), 133.46 (Ph-C), 134.99 (3'-CH), 135.25 (Ph-CH), 135.79 (Ph-CH) 135.99 (Ph-CH), 141.20 (6-CH), 150.99 (2-C), 163.45 (4-0);

MS (CI/NH$_3$., m/z); 449.1 (M+H$^+$, 50%), 466.2 (M+NH$_4^+$, 100%);

HRMS (ES+ve., M+H): Calculated for C$_{25}$H$_{28}$N$_2$O$_4$Si, requires 449.1896; found 449.1894.

IR$_{vmax}$/cm$^{-1}$ (film): 1697.3 (C=O).

R$_f$(10% MeOH/CHCl$_3$): 0.73.

Example 3

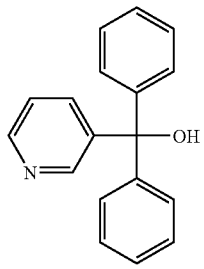

Diphenyl(pyridin-3-yl)methanol (3)

A solution of 3-bromopyridine (10 g, 0.063 mol) in dry THF (200 mL)/hexane (50 mL) was cooled to −90° C. To this cooled solution was added n-BuLi (2.2 M, 32 mL, 0.063 mol) slowly and allowed to stir for 30 min under N$_2$ atmosphere. A solution of benzophenone (11.5 g, 0.063 mol) in dry THF (50 mL) was added to this at the same temperature over a period of 30 min. The reaction mixture was warmed slowly to RT and allowed to stir another 3 h at RT. The reaction mixture was cooled, quenched with water (200 mL) and extracted with ethylacetate (2×100 mL). The organic layer was dried, concentrated under vacuum and crude purified by column chromatography over silica gel (30% ethyl acetate in petroleum ether) to give the title product (3.3 g).

Example 4

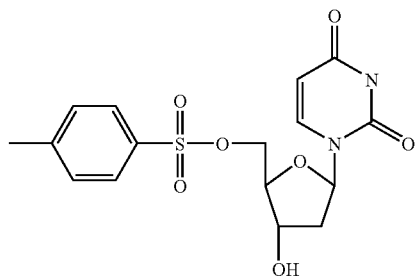

5'-O-Tosyl-2'-deoxyuridine (4)

To an ice-cold solution of 2'-deoxyuridine (5 g, 0.0219 mol) in dry pyridine (25 mL) tosyl chloride (5 g, 0.0263 mol) was added portion wise with stirring. The reaction mixture was stirred at 0° C. for 12 h. The reaction mixture was concentrated under vacuum and the crude residue was washed with diethyl ether (5×25 mL). The residue was further treated with water. The solid precipitate formed was filtered, washed with water (2×25 mL), diethyl ether (5×25 mL) and petroleum ether (5×25 mL). The solid was dried under vacuum and used for next reaction without any purification. Yield: 7.5 g, 89%.

TLC: CHCl$_3$/MeOH, 4:1, R$_f$=0.6

Example 5

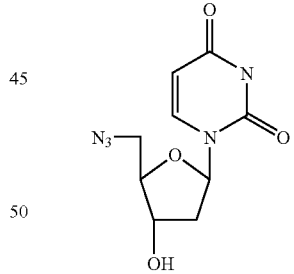

5'-Azido-2',5'-dideoxyuridine (5)

To a solution of 5'-O-tosyl-2'-deoxyuridine (13.591, 0.035 mol) in dry DMF (90 mL) was added NaN$_3$ (9.29 g, 0.141 mol) and the reaction mixture was allowed to stir at 95° C. for 12 h. The reaction mixture was cooled, the solid residue was removed by filtration and the filtrate was concentrated under vacuum to give the crude product. The crude was purified by column chromatography on silica gel (4% methanol in chloroform) which gave the title product (5.29 g, 56%) as a white solid.

TLC: CHCl$_2$/MeOH, 4:1, R$_f$=0.45

Example 6

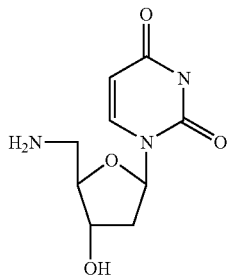

5'-Amino-2',5'-dideoxyuridine (6)

To a mixture of 5'-azido-2',5'-dideoxyuridine (5 g, 0.0197 mol) in methanol/water (150 mL, 1:1) was added Pd/C (0.25 g, 10%) under $N_2$ atmosphere and then hydrogenated for 4 h at RT. The reaction mixture was filtered through bed of celite and the filtrate was concentrated under vacuum. The solid obtained was washed with 3% methanol in chloroform which gave the title product (4.1 g, 89%) as an off-white solid.

TLC: $CHCl_3$/MeOH, 4:1, $R_f$=0.1.

Example 7

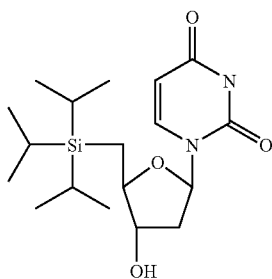

5'-O-Triisopropylsilyl-2'-deoxyuridine (7)

Imidazole (0.183 g, 2.69 mmol) was added to a solution of 2'-deoxyuridine (0.272 g, 1.19 mmol) in dry DMF (5 mL) under nitrogen. The mixture was cooled in an ice-salt bath before drop-wise addition of triisopropylsilyl chloride (0.28 mL, 1.31 mmol) via a syringe. The reaction mixture was kept at 0° C. for 3 h, allowed to warm up to room temperature and then stirred at room temperature for 22 h. After addition of water (5 mL), the crude mixture was extracted with $CHCl_3$ (2×10 mL). The organic layers were combined and dried over $MgSO_4$. Removal of the solvent under reduced pressure afforded a crude transparent oil which was further purified by flash chromatography eluting the column (ISOLUTE SI) a gradient of 0→10% $CH_3OH$ in $CHCl_3$. The title compound was obtained from the fractions with $R_f$=0.25 (10% $CH_3OH$ in $CHCl_3$) as a crystalline white solid (0.366 g, 74%). M.p. 152-153° C.

$^1$H NMR (300 MHz, $CDCl_3$) δ 1.08 (21H, m, iPr—H), 2.18 (1H, m, 2'-H), 2.49 (1H, m, 2'-H), 3.97 (2H, m, 5'-H), 4.08 (1H, m, 4'-H), 4.56 (1H, m, 3'-H), 5.70 (1H, d, J=8.1 Hz, 5-H), 6.38 (1H, t, J=6.2 Hz, 1'-H), 7.96 (1H, d, J=8.1 Hz, 6-H), 10.16 (1H, bs, 3-NH).

$^{13}$C NMR (75 MHz, $CDCl_3$) δ 12.7 (iPr—CH), 18.4 (iPr—$CH_3$), 41.9 (2'-$CH_2$), 63.8 (5'-$CH_2$), 71.7 (3'-CH), 85.7 (1'-CH), 88.0 (4'-CH), 102.5 (5-CH), 140.9 (6-CH), 151.1 (2-C), 164.5 (4-C).

$ES^+$ m/z (%) 790 ([2M+Na]$^+$, 10), 407 ([M+Na]$^+$, 100).

HRMS ($ES^+$) Found [M+Na]$^+$ 407.1988; $C_{18}H_{32}N_2O_5SiNa^+$ requires 407.1973.

Anal. Calcd for $C_{18}H_{32}N_2O_5Si$ (%) C, 56.22; H, 8.39; N, 7.28. found C, 56.07; H, 8.50; N, 7.18.

Example 8

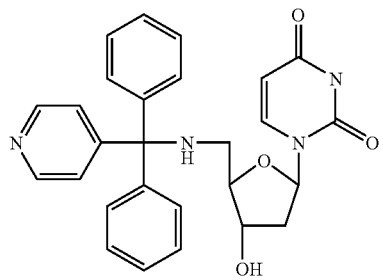

5'-(4-pyridyldiphenylmethyl)amino-2',5'-dideoxyuridine (8)

5'-Amino-2',5'-dideoxyuridine (0.108 g, 0.475 mmol) was added to a solution of diphenyl(4-pyridyl)chloromethane hydrochloride (0.150 g, 0.474 mmol), pyridine (3 mL) and $Et_3N$ (0.12 mL, 0.862 mmol). The reaction mixture was heated at 40° C. for 4 h then the temperature was increased to 70° C. for 10 h. The crude solution was partitioned between water (5 mL) and EtOAc (3×7 mL). The organic extracts were combined, dried over $Na_2SO_4$ and concentrated in vacuo. The brown solid obtained was taken in MeOH and the remaining insoluble material was filtered off. The filtrate was concentrated under reduced pressure and further purified by flash column chromatography (ISOLUTE SI column) using a gradient elution of 0→8% MeOH in $CHCl_3$. The fractions with $R_f$=0.24 (10% MeOH/$CHCl_3$) afforded the title compound as a pale yellow solid (61 mg, 27%).

$^1$H NMR (300 MHz, $CD_3OD$) δ 2.15-2.60 (4H, m, 2',5'-H), 4.03 (1H, m, 3'-H or 4'-H), 4.18 (1H, m, 3'-H or 4'-H), 5.63 (1H, d, J=8.0 Hz, 5-H), 6.21 (1H, t, J=6.4 Hz, 1'-H), 7.20-7.48 (11H, m, 6-H and Ph-H), 7.59 (2H, d, J=5.9 Hz, 4"-H), 8.42 (2H, d, J=5.9 Hz, 5"-H).

$^{13}$C NMR (75 MHz, $CD_3OD$) δ 40.9 (2'-$CH_2$), 47.6 (5'-$CH_2$), 722 (2'-C), 73.3 (3'-CH), 87.1 (1'-CH or 4'-CH), 87.9 (1'-CH or 4'-CH), 103.4 (5-CH), 125.7 (4"-CH), 128.6 (Ph-CH), 129.7 (Ph-CH), 130.2 (Ph-CH), 130.3 (Ph-CH), 142.7 (6-CH), 145.8 (Ph-C), 146.1 (Ph-C), 150.2 (5"-C), 152.4 (3"-C), 158.1 (2-C), 166.4 (4-C).

$ES^+$ m/z (%) 963 ([2M+Na]$^+$, 13), 493 ([M+Na]$^+$, 84), 471 ([M+H]$^+$, 13).

HRMS (ES+) Found [M+H]+ 471.2033; $C_{27}H_{27}N_4O_4^+$ requires 471.2027.

M.p. 131-133° C.

Example 9

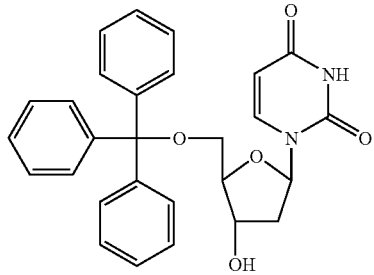

5'-O-trityl-2'-deoxyuridine (9)

2'-Deoxyuridine (1.00 g, 4.39 mmol) and triphenylmethylchloride (1.34 g, 4.83 mmol) were stirred in dry pyridine (20 ml) overnight at 50° C. under an atmosphere of nitrogen. The reaction mixture was then poured into ice-H$_2$O (100 ml) with vigorous stirring and filtered. The precipitate was dissolved in EtOAc (100 ml) and the solution was washed with 0.5M HCl (100 ml) and H$_2$O (100 ml), dried (Na$_2$SO$_4$) and reduced in vacuo. The residue was washed with toluene to leave the title compound (1.99 g, 97%) as a pale yellow solid. For analytical purposes, the compound was purified by gradient flash column chromatography, eluting with 5→10% MeOH/CHCl$_3$.

$^1$H NMR (300 MHz; CDCl$_3$): δ 2.34 (1H, m, 2'-H), 2.45 (1H, m, 2'-H), 3.51 (2H, ddd, J=3.5, 8.6, 10.6 Hz, 5'-H), 4.12 (1H, dd, J=3.6, 7.2 Hz, 4'-H), 4.64 (1H, m, 3'-H), 5.47 (1H, d, J=8.1 Hz, 5-H), 6.40 (1H, t, J=6.3 Hz, 1'H), 7.22-7.49 (15H, m, Ph-H), 7.86 (1H, d, J=8.1 Hz, 6-H), 9.37 (1H, s, 3-NH);

$^{13}$C NMR (75 MHz; CDCl$_3$): δ 41.60 (2'-CH$_2$), 63.53 (5'-CH$_2$), 71.84 (3'-CH), 85.49 (4'-CH), 86.43 (1'-CH), 88.03 (Ph$_3$C), 127.92 (Ph-CH), 128.68 (Ph-CH), 129.49 (Ph-CH), 140.69 (6-CH), 143.67 (Ph-CH), 153.24 (2-C), 163.93 (4-C).

MS (AP+., m/z): 243 (Tr+, 100%); R$_f$ (10% MeOH/CHCl$_3$): 0.49;

Example 10

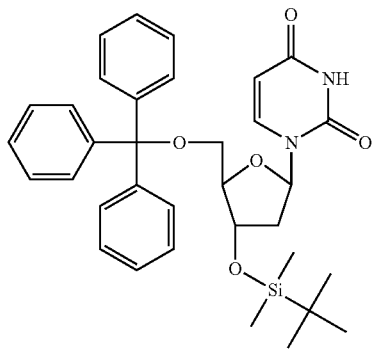

1-[4-(tert-Butyl-dimethyl-silanyloxy)-5-trityloxymethyl-tetrahydro-furan-2-yl]-1H pyrimidine-2,4-dione or 3'-O-tert-Butylsilyl-5'-O-trityl-2'-deoxyuridine (10)

5'-O-trityl-2'deoxyuridine (0.70 g, 1.49 mmol) in dry DMF (3 ml) was added drop-wise under an atmosphere of nitrogen, with ice bath cooling, to a stirred solution of tert-butyldimethylsilyl chloride (0.25 g, 1.65 mmol) and imidazole (0.22 g, 3.28 mmol) in dry DMF (3 ml). The mixture was allowed to warm to room temperature and stirred overnight H$_2$O (10 ml) was added (10 ml) and the mixture was extracted with Et$_2$O (2×50 ml). The combined extracts were washed with saturated NaHCO$_3$ (50 ml) and H$_2$O (50 ml), dried (Na$_2$SO$_4$) and reduced in vacuo. A flash silica column eluting with 3% MeOH/CHCl$_3$ gave the title compound (0.65 g, 74%) as white foam.

$^1$H NMR (300 MHz; CDCl$_3$): δ −0.05 [3H, s, Si(CH$_3$)$_2$] and 0.00 [3H, s, Si(CH$_3$)$_2$], 0.85 [9H, s, C(CH$_3$)$_3$], 2.12-2.20 (1H, m, 2'-H), 2.31-2.39 (1H, m, 2'-H), 3.33 (1H, dd, J=2.8, 10.7 Hz, 5'-H), 3.46 (1H, dd, J=2.9, 10.7 Hz, 5'-H), 3.92 (1H, dt, J=2.8, 4.4 Hz, 4'-H), 4.51 (1H, dd, J=4.9, 10.9 Hz, 3'-H), 5.34 (1H, d, J=8.1 Hz, 5-H), 6.26 (1H, t, J=6.0 Hz, 1'-H), 7.23-7.39 (15H, m, Ph-H), 7.85 (1H, d, J=8.1 Hz, 6-H), 9.11 (1H, s, 3-NH);

$^{13}$C NMR (75 MHz; CDCl$_3$): −4.49 and −4.20 (Si(CH$_3$)$_2$), 18.37[C(CH(CH$_3$)$_3$], 22.06 and 26.17 [C(CH$_3$)$_3$], 42.23 (2'-CH$_2$), 62.27 (5'-CH$_2$), 71.38 (3'-CH), 85.55 (4'-CH) 86.83 (1'-CH), 87.89 (Ph$_3$C), 102.70 (5-CH), 127.91 (Ph-CH), 128.48 (Ph-CH), 129.15 (Ph-CH), 140.62 (6-CH), 143.59 (Ph-CH), 150.68 (2-C), 163.81 (4-C);

MS (AP+., m/z): 243 (Tr+, 50%), 341 (M-Tr+, 75%), 607 (M+Na+, 100%)

R$_f$ (3% MeOH/CHCl$_3$): 0.33;

Example 11

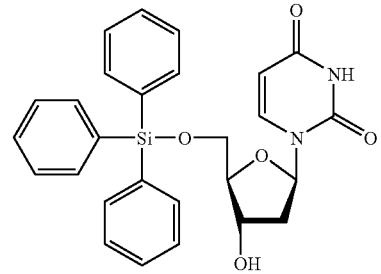

5'-O-Triphenylsilyl-2'-deoxyuridine (11)

A solution of triphenylsilyl chloride (0.437 g, 1.48 mmol) in dry pyridine (4 mL) was added drop-wise to a solution of 2'-deoxyuridine (0.278 g, 1.22 mmol) in dry pyridine (4 mL) previously cooled in an ice-salt bath. The reaction mixture was kept at 0° C. for 1 h. The reaction was monitored by TLC (10% CH$_3$OH in CHCl$_3$) and quenched with CH$_3$OH (50 L). The solvent was removed under reduced pressure to give a crude yellow liquid which was further purified by silica gel column chromatography (Isolute SI column) using a gradient elution of 0→10% CH$_3$OH in CHCl$_3$. The fractions with R$_f$=0.30 (10% CH$_3$OH/CHCl$_3$) were combined and concentrated to yield the title compound as a white crystalline solid (0.506 g, 85%).

¹H NMR (300 MHz, CDCl₃) δ 2.25 (1H, m, 2'-H), 2.44 (1H, m, 2'-H), 2.95 (1H, bs, 3'-OH), 3.93-4.27 (3H, m, 5'-H and 4'-H), 4.60 (1H, m, 3'-H), 5.19 (1H, d, J=8.2 Hz, 5-H), 6.41 (1H, t, J=6.4 Hz, 1'-H), 7.35-7.73 (15H, m, Ph-H), 7.80 (1H, d, J=8.1 Hz, 6-H), 9.46 (1H, bs, 3-NH).

¹³C NMR (75 MHz, CDCl₃) δ 41.6 (2'-CH₂), 63.8 (5'-CH₂), 71.7 (3'-CH), 85.3 (1'-CH), 87.3 (4'-CH), 102.7 (5-CH), 128.6 (Ph-CH), 131.1 (Ph-CH), 133.3 (Ph-C), 135.8 (Ph-CH), 140.5 (6-CH), 150.9 (2-C), 163.9 (4-C).

ES⁺ m/z (%) 509 ([M+Na]⁺, 100).

ES⁺ m/z (%) 509 ([M+Na]⁺, 78), 151 (100).

HRMS (ES⁺) Found [M+Na]⁺ 509.1504; C₂₇H₂₆N₂O₅Si requires 509.1503.

Anal. calcd for C₂₇H₂₆N₂O₅Si (%): 0.32 HCl C, 65.09; H, 5.32; N, 5.62. found: C, 65.01; H, 5.27; N, 5.62.

Example 12

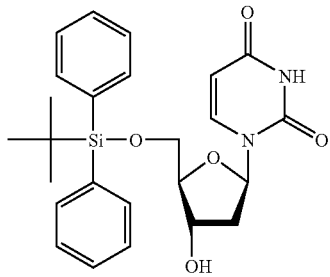

5'-O-tert-Butyldiphenylsilyl-2'-deoxyuridine (12)

2'-Deoxyuridine (0.530 g, 2.32 mmol) was dissolved in dry DMF (5 mL) under nitrogen and the solution was cooled in an ice-salt bath. A solution of tert-butyldiphenylsilyl chloride (0.710 g, 2.58 mmol) and imidazole (0.342 g, 5.69 mmol) in dry DMF (4 mL) was then added drop-wise. The reaction mixture was stirred at 0° C. for 2 h and then at room temperature for 15 h. The reaction was quenched by addition of water (15 mL). The crude mixture was extracted with CHCl₃ (2×15 mL). The organic layers were combined, dried over MgSO₄ and concentrated in vacuo to give a transparent oil (0.419 g). This oil was chromatographed on a silica gel column (Isolute SI column) eluted with a gradient of 0→0% CH₃OH in CHCl₃. The fractions with R$_f$=0.26 (10% CH₃OH/CHCl₃) were gathered and concentrated to afford the title compound as a white crystalline solid (0.823 g, 76%).

¹H NMR (300 MHz, CDCl₃) δ 1.14 (9H, m, tBu-H), 2.27 (1H, m, 2'-H), 2.50 (1H, m, 2'-H), 2.69 (1H, bs, 3'-OH), 3.90 (1H, m, 4'-H), 4.05 (2H, m, 5'-H), 4.60 (1H, m, 3'-H), 5.52 (1H, d, J=8.1 Hz, 5-H), 6.41 (1H, t, J=6.4 Hz, 1'-H), 7.48 (6H, m, Ph-H), 7.70 (4H, m, Ph-H), 7.87 (1H, d, J=8.1 Hz, 6-H), 9.34 (1H, bs, 3-NH).

¹³C NMR (75 MHz, CDCl₃) δ 19.7 (tBu-C), 27.4 (tBu-CH₃), 41.7 (2'-CH₂), 64.1 (5'-CH₂), 71.9 (3'-CH), 85.4 (1'-CH), 87.5 (4'-CH), 102.6 (5-CH), 128.4 (Ph-CH), 128.5 (Ph-CH), 130.6 (Ph-CH), 132.7 (Ph-C), 133.1 (Ph-C), 135.8 (Ph-CH), 136.0 (Ph-CH), 140.5 (6-CH), 150.9 (2-C), 163.9 (4-C).

ES⁺ m/z (%) 489 ([M+Na]⁺, 100).

Anal. calcd for C₂₅H₃₀N₂O₅Si 0.58(%): HCl C, 61.56; H, 6.32; N, 5.74. found C, 61.61; H, 6.23; N, 5.72.

Example 13

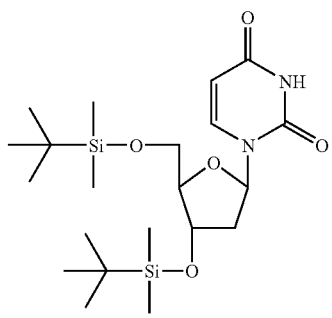

3',5'-O-bistertbutyldimethylsilyl-2'-deoxyuridine

A solution of t-butyl dimethylsilylchloride (2.18 g, 14.46 mmol) and imidazole (1.07 g, 28.92 mmol) in DMF (30 ml) was added slowly (drop wise) to a stirred solution of 2'-deoxyuridine (3 g, 13.15 mmol) in dry DMF (40 ml), with ice-bath cooling at 0° C., under atmosphere of nitrogen.

After 2 hours, H₂O (100 ml) was added and the mixture was extracted with AcOEt (3×100 ml). The combined extracts were washed with saturated NaHCO₃ (2×100 ml), dried (MgSO₄) and concentrated. The residue was purified by flash chromatography and the title compound was isolated as a white amorphous solid from the fractions with Rf=0.65 (10% CH₃OH in CHCl₃).

¹H-NMR (300 MHz, CDCl₃) δ 0.2 (s, 12H, tBu[CH₃]₂Si), 1.0 (s, 18H, tBu[CH₃]₂Si), 2.5 (1H, m, 2'-H), 2.2 (1H, m, 2'-H), 3.06 (1H, d, J=5.0 Hz, 3'-H), 3.95 (1H, dd, J=11.5 Hz, 2.2 Hz, 5'-H), 4.01 (1H, dd, J=11.5, 2.6 Hz, 5'-H), 4.15 (1H, m, 4'-H), 5.78 (1H, d, J=8.23 Hz, 5-H), 6.45 (1H, t, J=6.95 Hz, 1'-H), 8.02 (1H, d, J=8.2 Hz, 6-H), 9.5 (1H, s, 3-NH).

¹³C-NMR (75 MHz, CDCl₃) δ 163.9 (4-C). 150.9 (2-C). 140.8 (6-CH). 102.7 (5-CH), 87.9 (4'-CH), 85.8 (1'-CH), 72.5 (3'-CH), 63.7 (5'-CH₂) 42.0 (2'-CH₂), 26.3 (CH₃). 18.8 (CH₃).

Example 14

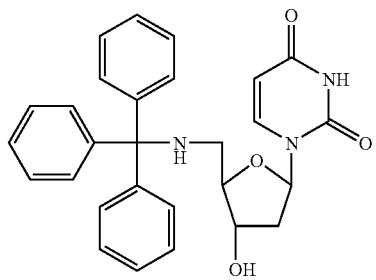

5'-Tritylamino-2',5'-dideoxyuridine (14)

5'-Amino-2',5'-dideoxyuridine (0.200 g, 0.88 mmol) was taken in dry pyridine (5 mL) and the mixture was sonicated for a few minutes. Trityl chloride (0.278 g, 1.00 mmol) was added and the reaction mixture was stirred at 50° C. overnight. The reaction was then quenched with water (20 mL). The crude mixture was extracted with DCM (3×10 mL). The organic layers were combined, washed with water (10 mL), dried over MgSO$_4$ and concentrated on the rotary evaporator. The resultant brown oil was further purified by silica gel column chromatography (Isolute Si column) using a gradient elution of 0→10% CH$_3$OH in CHCl$_3$. The fractions with R$_f$=0.28 (10% CH$_3$OH/CHCl$_3$) were pooled and evaporated to dryness to yield the title compound as a white solid (0.202 g, 49%).

$^1$H NMR (300 MHz, CDCl$_3$) δ 2.07 (2H, m, 2, —H), 2.28-2.53 (2H, m, 5'-H), 2.73 (1H, dd, J=3.5, 12.1 Hz, 1"-NH), 2.97 (1H, bs, 3'-OH), 4.19 (1H, m, 4'-H), 4.33 (1H, m, 3-H), 5.72 (1H, d, J=8.1 Hz, 5-H), 6.36 (1H, t, J=6.4 Hz, 1'-H), 7.14 (1H, d, J=8.1 Hz, 6-H), 7.23-7.43 (9H, m, Ph-H), 7.57 (6H, m, Ph-CH), 9.47 (1H, bs, 3-NH).

$^{13}$C NMR (75 MHz, CDCl$_3$) δ 40.8 (2'-CH$_2$), 46.6 (5'-CH$_2$), 71.1 (2"-C), 73.0 (3'-CH), 85.4 (1'-CH), 86.7 (4'-CH), 103.2 (5-CH), 127.0 (Ph-CH), 128.4 (Ph-CH), 129.0 (Ph-CH), 139.8 (6-CH), 145.8 (Ph-C), 150.7 (2-C), 163.7 (4-C).

ES$^+$ m/z (%) 243 (Ph$_3$C$^+$, 100), 470 ([M+H]$^+$, 4), 492 ([M+Na]$^+$, 23).

HRMS (ES$^+$) Found [M+H]$^+$ 470.2076; C$_{28}$H$_{28}$N$_3$O$_4$ requires 470.2074.

M.p. 132-134° C.

Anal calcd for C$_{28}$H$_{27}$N$_3$O$_4$(%): 0.53 HCl C, 68.79; H, 5.68; N, 8.60. found: C, 68.79, H, 5.55; N, 8.59.

Example 15

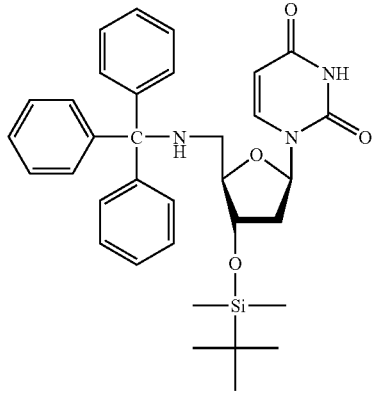

3'-O-tertbutyldimethylsilyl-5'-Tritylamino-2',5-dideoxyuridine (15)

A solution of 5'-tritylamino-2',5'-dideoxyuridine (0.172 g, 0.37 mmol) in anhydrous DMF (2 mL) was added drop-wise to an ice cold solution of tert-butyl dimethylsilyl chloride (68 mg, 0.45 mmol) and imidazole (60 mg, 0.88 mmol) in anhydrous DMF (2 mL). The reaction mixture was stirred at 0° C. for 2 h and at room temperature for a further 20 h. It was then partitioned between water (10 mL) and Et$_2$O (2×20 mL). The combined organic layers were washed with a saturated aqueous solution of NaHCO$_3$ (15 mL), dried over MgSO$_4$ and concentrated in vacuo. The resultant white solid was further purified by column chromatography (Isolute Si column) using a gradient elution of 0→10% CH$_3$OH in CHCl$_3$. The fractions with R$_f$=0.69 (10% CH$_3$OH/CHCl$_3$) were pooled and evaporated to dryness to yield the title compound as a white solid (154 mg, 72%).

$^1$H NMR (300 MHz, CDCl$_3$) δ 0.00-0.02 (6H, 2×s, Si(CH$_3$), 0.86 (9H, s, C(CH$_3$)$_3$), 1.90 (2H, m, 2'-H), 2.11-2.35 (2H, m, 5'-H), 2.59 (1H, bd, J=13 Hz, 1"-NH), 4.06 (2H, m, 3'-H and 4'-H), 5.65 (1H, d, J=8.1 Hz, 5-H), 6.25 (1H, t, J=6.3 Hz, 1'-H), 7.07 (1H, d, J=8.1 Hz, 6-H), 7.14-7.37 (9H, m, Ph-H), 7.48 (6H, m).

$^{13}$C NMR (75 MHz, CDCl$_3$) δ −4.4 (SiCH$_3$), −4.2 (SiCH$_3$), 18.4 (C(CH$_3$)$_3$), 26.1 (C(CH$_3$)$_3$), 41.4 (2'-CH$_2$), 46.5 (5'-CH$_2$), 71.2 (2"-C), 73.3 (3'-CH), 85.6 (1'-CH), 87.3 (4'-CH), 103.1 (5-CH), 127.0 (Ph-CH), 128.4 (Ph-CH), 129.0 (Ph-CH), 139.7 (6-CH), 145.9 (Ph-C), 150.6 (2-C), 163.7 (4-C).

ES$^+$ m/z (%) 584 ([M+H]$^+$), 606 ([M+Na]$^+$).

HRMS (ES$^+$) Found [M+H]$^+$ 584.2938; C$_{34}$H$_{42}$N$_3$O$_4$Si requires 584.2939.

Example 16

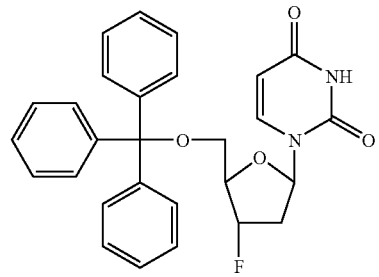

1-(4-Fluoro-5-trityloxymethyl-tetrahydro-furan-2-yl) 2,3-dihydro-1H-pyrimidin-4-one or 3'-Fluoro-5'-O-trityl-2',3'-dideoxyuridine (16)

3'-Fluoro-2',3'-dideoxyuridine (0.3 g, 1.30 mmol) and triphenylmethyl chloride (0.44 g, 1.57 mmol) were stirred in dry pyridine (20 ml) overnight at 50° C. under an atmosphere of nitrogen. The reaction mixture was then poured into ice-H$_2$O (50 ml) with vigorous stirring and filtered. The precipitate was dissolved in EtOAc (50 ml) and the solution was washed with 0.5M HCl (50 ml) and H$_2$O (50 ml) dried (Na$_2$SO$_4$) and reduced in vacuo to obtain a crude product, which was purified by gradient flash column chromatography eluting with 2→6% MeOH/CHCl$_3$ to obtain the title compound as a white solid (0.48 g, 77%).

$^1$H NMR (300 MHz; CDCl$_3$): δ 2.27-2.50 (1H, m, 2'-H), 2.78-2.92 (1H, m, 2'-H), 3.53-3.63 (2H, m, 5'H), 4.41-4.51 (1H, d, J=27.3 Hz, 4'-H), 5.33-5.53 (2H, m, 3', 5-H), 6.50-6.55 (1H, m, 1'-H), 7.46 (15H, m, Ph-H), 7.80 (1H, d, J 8.1, 6-H);

$^{13}$C NMR (75 MHz; CDCl$_3$): δ 39.43 and 39.71 (2'-CH$_2$), 63.75 and 63.89 (5'-CH$_2$), 84.54 and 84.88 (4'-CH), 85.38 (1'-CH), 88.27 (Ph-C)—, 93.44 (Ph-CH), 95.80 (Ph-CH), J 178.48, 3'-CH), 103.08 (5-CH), 128.06 (Ph-CH), 128.58 (Ph-CH), 129.00 (Ph-CH), 140.18 (6-CH), 143.31 (Ph-C), 150.67 (2-C), 163.53 (4-C);

$^{19}$F NMR (282 MHz; CDCl$_3$): δ −174.26;

MS (Cl/NH$_3$., m/z): 473.2 (M+H$^+$, 50%), 490.3 (M+NH$_4^+$, 80%);

HRMS (EI., M$^+$): Calculated for C$_{20}$H$_{25}$N$_2$O$_4$F, requires 472.1798; found 472.1797.

IR$_{vmax}$/cm$^{-1}$ (KBr): 703 (s) and 763 (s) (Aromatic, monosubstituted), 1107.9 (C—F), 1689.3 (C=O) and 1702.3 (C=O). R$_f$(10% MeOH/CHCl$_3$): 0.52.

Mp: 128-130° C.

Example 17

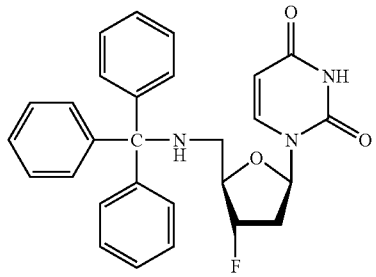

3'-Fluoro-5'-tritylamino-2',3',5'-trideoxyuridine (17)

The title compound was obtained as a light yellow crystalline solid (91 mg, 32%) from the reaction of the corresponding amine (0.137 g, 0.59 mmol) and trityl chloride (0.199 g, 0.66 mmol) in dry pyridine (4 mL). The procedure was similar to that followed for the preparation of the 3' hydroxy analogue 5'-tritylamino-2',5'-dideoxyuridine (WSP871, see example 14).

$^1$H NMR (300 MHz, CDCl$_3$) δ 1.87-2.13 (2H, m, 2'-H), 2.28 (1H, dd, J=8.1, 12.0 Hz, 1"—NH), 2.57-2.78 (2H, m, 5'-H), 4.48 (1H, dm, J=25 Hz, 4'-H), 5.11 (1H, dd, J=5.3, 53.7 Hz, 3'-H), 5.71 (1H, d, J=8.1 Hz, 5-H), 6.37 (1H, dd, J=5.6, 8.7 Hz, 1'-H), 6.98 (1H, d, J=8.1 Hz, 6-H), 7.23-7.43 (9H, m, Ph-H), 7.53 (6H, m, Ph-CH), 9.39 (1H, s, 3-NH).

$^{13}$C NMR (75 MHz, CDCl$_3$) δ 38.5 (d, J=21.8 Hz, 2'-CH$_2$), 46.1 (d, J=9.2 Hz, 5'-CH$_2$), 71.1 (Ph$_3$C), 85.2 (d, J=25.3 Hz, 4'-CH), 85.5 (1'-CH), 94.4 (d, J=179.9 Hz, 3'-CH), 103.6 (5-CH), 127.1 (Ph-CH), 128.5 (Ph-CH), 128.9 (Ph-CH), 139.3 (6-CH), 145.7 (Ph-C), 150.5 (2-C), 163.4 (4-C).

$^{19}$F NMR (282 MHz, CDCl$_3$) δ −175.7 (m, 3'-F).

ES$^+$ m/z (%) 243 (Ph$_3$C$^+$, 93), 494 ([M+Na]$^+$, 92).

Example 18

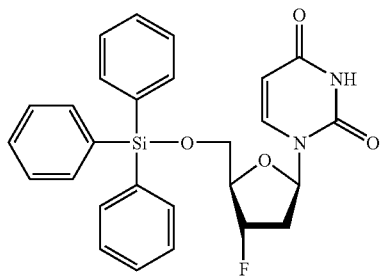

3'-Fluoro-5'-O-triphenylsilyl-2',3'-dideoxyuridine (18)

The title compound was synthesised following a similar procedure as described for Example 11. 3'-Fluoro-2',3'-dideoxyuridine (0.214 g, 0.93 mmol) was reacted with triphenylsilyl chloride (0.332 g, 1.12 mmol) in dry pyridine (7 mL) for 3 h. to yield the title compound as a white solid (0.274 g, 60%).

$^1$H NMR (300 MHz, CDCl$_3$) δ 2.19 (1H, m, 2'-H), 2.67 (1H, m, 25-H), 4.11 (2H, m, 5'-OH), 4.36 (1H, d, J=27.1 Hz, 3'-H), 5.22 (1.5H, m, 4'-H and 5-H), 5.40 (0.5H, d, J=4.8 Hz, 4'-H), 6.50 (1H, dd, J=5.4, 9.1 Hz, 1'-H), 7.41-7.75 (16H, m, 6-H and Ph-H), 9.04 (1H, bs, 3-NH).

$^{13}$C NMR (75 MHz, CDCl$_3$) δ 39.5 (d, J=20.7 Hz, 2'-CH$_2$), 64.3 (d, J=11.5 Hz, 5'-CH$_2$), 85.2 (1'-CH), 85.4 (d, J=24.7 Hz, 4'-CH), 94.9 (d, J=178.7 Hz, 3'-CH), 103.1 (5-CH), 128.8 (Ph-CH), 131.2 (Ph-CH), 133.0 (Ph-C), 135.7 (Ph-CH), 140.1 (6-CH), 150.7 (2-C), 163.5 (4-C).

$^{19}$F NMR (282 MHz, CDCl$_3$) δ −175.1 (m, 3'-F).

ES$^+$ m/z (%) 511 ([M+Na]), 5), 87 (100).

ES$^-$ m/z (%) 487 ([M−H$^+$], 31), 75 (100).

Example 19

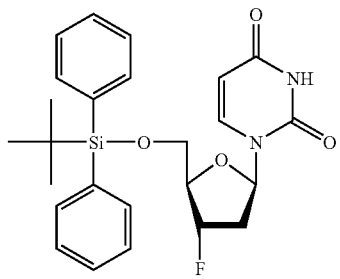

3'-Fluoro-5'-O-tert-Butyidiphenylsilyl-2',3'-dideoxyuridine (19)

The title compound was synthesised following a similar procedure as described for Example 12. 3'-Fluoro-2',3'-dideoxyuridine (0.176 g, 0.77 mmol) was reacted with tert-butyldiphenylsilyl chloride (0.238 g, 0.87 mmol) and imidazole (0.116 g, 1.70 mmol) in dry DMF (4 mL) for 3 h. Compound WSP948 was obtained as a white solid (0.331 g, 92%).

$^1$H NMR (300 MHz, CDCl$_3$) δ 1.17 (9H, m, tBu-H), 2.24 (1H, m, 2'-H), 2.78 (1H, m, 2'-H), 4.00 (2H, m, 5'-H), 4.38 (1H, d, J=26.7 Hz, 4'-H), 5.34 (1H, dd, J=4.9, 53.8 Hz, 3'-H), 5.56 (1H, d, J=8.1 Hz, 5-H), 6.51 (1H, m, 1'-H), 7.43-7.60 (6H, m, Ph-H), 7.65-7.74 (4H, m, Ph-H), 7.27 (1H, d, J=8.1 Hz, 6-H), 9.11 (1H, bs, 3-NH).

$^{13}$C NMR (75 MHz, CDCl$_3$) δ 19.7 (tBu-C), 27.4 (tBu-CH$_3$), 39.7 (d, J=21.3 Hz, 2'-CH$_2$), 64.1 (d, J=10.9 Hz, 5'-CH$_2$), 85.4 (1'-CH), 85.6 (d, J=24.7 Hz, 4'-CH), 94.7 (d, J=178.7 Hz, 3'-CH), 103.2 (5-CH), 128.5 (Ph-CH), 128.6 (Ph-CH), 130.7 (Ph-CH), 132.2 (Ph-C), 132.8 (Ph-C), 135.7 (Ph-CH), 136.0 (Ph-CH), 140.0 (6-CH), 150.6 (2-C), 163.5 (4-C).

$^{19}$F NMR (282 MHz, CDCl$_3$) δ −175.5 (m, 3'-F).

ES$^-$ m/z (%) 467 ([M−H$^+$], 53), 75 (100).

Example 20

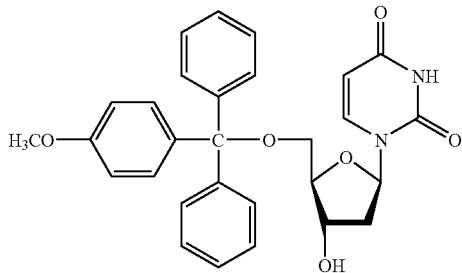

5'-O-paramethoxytrityl-2'-deoxyuridine (20)

4-Methoxytrityl (0.610 g, 1.98 mmol) was added to a solution of 2'-deoxyuridine (0.4109, 1.80 mmol) in anhydrous pyridine (10 mL). The reaction mixture was stirred at 50° C. for 40 h. The crude mixture was partitioned between water (40 mL) and DCM (2×40 mL). The organic layers were combined, washed with water (2×80 mL), dried over MgSO$_4$ and concentrated in vacuo. The resultant yellow oil was further purified by silica gel column chromatography (using Jones Chromatography Isolute SI columns). The column was eluted with a gradient of 0→5% CH$_3$OH in CHCl$_3$. The fractions with R$_f$=0.28 (10% CH$_3$OH/CHCl$_3$) yielded the title compound as a white crystalline solid (0.625 g, 69%).

$^1$H NMR (300 MHz, CDCl$_3$) δ 2.27 (1H, m, 5'-H), 2.42 (1H, m, 5'-H), 2.57 (1H, bs, 3'-OH), 3.42 (2H, m, 2'-H), 3.76 (3H, s, OCH$_3$), 4.00 (1H, m, 4'-H), 4.54 (1H, m, 3'-H), 5.37 (1H, d, J=8.1 Hz, 5-H), 6.29 (1H, t, J=6.3 Hz, 1'-H), 6.82 (2H, m, Ar—H), 7.18-7.38 (12H, m, Ar—H), 7.74 (1H, d, J=8.1 Hz, 6-H), 9.20 (1H, bs, 3-NH).

$^{13}$C NMR (75 MHz, CDCl$_3$) δ 41.6 (2'-CH$_2$), 55.7 (OCH$_3$), 63.5 (5'-CH$_2$), 71.9 (3'-CH), 85.5 (4'-CH), 86.5 (1'-CH), 87.8 (Ar$_3$C), 102.7 (5-CH), 113.8 (Ar—CH), 127.7 (Ar—CH), 128.5 (Ar—CH), 128.8 (Ar—CH), 130.8 (Ar—CH), 135.1 (Ar—C), 140.6 (6-CH), 144.1 (Ar—C), 144.3 (Ar—C), 150.8 (2-C), 159.3 (Ar—C), 163.7 (4-C).

ES$^+$ m/z (%) 523 ([M+Na]$^+$, 100)

HRMS (ES$^+$) Found [M+Na]$^+$ 523.1848; C$_{29}$H$_{28}$N$_2$O$_6$Na requires 523.1845.

IR (KBr) 3208, 3054, 1714, 1694, 1682, 1507, 1470, 1250, 1092, 1035, 759 cm$^{-1}$.

M.p. 96-97° C.

Anal calcd for C$_{29}$H$_{28}$N$_2$O$_6$(%): 1.43 HCl, 0.40H$_2$O C. 62.21, H, 5.44; N, 5.00; Cl, 9.06. found: C, 62.17; H, 5.05; N, 4.85; Cl, 8.86.

Example 21

5'-O-(4-cyanotrityl)-2'-deoxyuridine (21)

4-Cyanotrityl (0.397 g, 1.31 mmol) was added to a solution of 2'-deoxyuridine (0.229 g, 1.00 mmol) in dry pyridine (5 mL). As the reaction was not complete after 72 h at 50° C., DMAP (11 mg, 0.09 mmol) was added and the reaction mixture was kept at 50° C. for a further 20 h. H$_2$O (20 mL) was added and the crude mixture was extracted with DCM (2×15 mL and 10 mL). The combined organic layers were dried over Na$_2$SO$_4$, concentrated in vacuo and purified by flash column chromatography eluting the column (ISOLUTE SI) with a gradient of 0→6% CH$_3$OH in CHCl$_3$. The fractions with R$_f$=0.29 (10% CH$_3$OH/CHCl$_3$) afforded the title compound as a white solid (0.215 g, 43%).

$^1$H NMR (300 MHz, CDCl$_3$) δ 2.19 (1H, m, 2'-CHH), 2.45 (1H, m, 2'-CH H), 2.94 (1H, bs, 3'-OH), 3.38 (2H, m, 5'-H), 4.06 (1H, m, 4'-H), 4.50 (1H, m, 3'-H), 5.45 (1H, d, J=8.1 Hz, 5-H), 6.27 (1H, t, J=6.2 Hz, 1'-H), 7.24-7.34 (10H, m, Ph-H), 7.53-7.60 (5H, m, 6-H and Ar—H), 9.50 (1H, bs, 3-NH).

$^{13}$C NMR (75 MHz, CDCl$_3$) δ 41.4 (2'-CH$_2$), 63.9 (5'-CH$_2$), 71.7 (3'-CH), 85.6 (1'-CH), 86.1 (4'-CH), 87.6 (ArPh$_2$C), 102.8 (5-CH), 111.4 (Ar—C), 119.0 (C≡N), 128.6 (Ph-CH), 128.8 (Ph-CH), 129.0 (Ar—CH), 132.4 (Ar—CH), 140.3 (6-CH), 142.0 (Ph-C), 142.1 (Ph-C), 150.1 (Ar—C), 150.8 (2-C), 163.8 (4-C).

ES$^+$ m/z (%) 518 ([M+Na]$^+$, 23), 268 (CNTr$^+$, 100).

ES$^-$ m/z (%) 494 (M–H$^+$, 100).

HRMS (ES$^+$) Found [M+NH$_4$]+ 513.2132; C$_{29}$H$_{29}$N$_4$O$_5$$^+$ requires 513.2132.

M.p. 92-95° C.

IR (KBr) 3401, 3180, 3060, 2230 (CN), 1685, 1463, 1273, 1088 cm$^{-1}$.

Anal calcd for C$_{29}$H$_{25}$N$_3$O$_5$(%): 2.35 HCl C, 59.93; H, 4.74; N, 7.23. found: C, 59.89; H, 4.45; N, 7.02.

Example 22

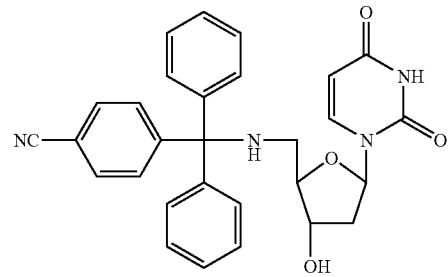

5'-[(4-cyanotrityl)amino]-2',5'-dideoxyuridine (22)

4-Cyanotrityl chloride (0.406 g, 1.34 mmol) was added to a solution of 5'-amino-2',5'-dideoxyuridine (0.239 g, 1.05 mmol) in dry pyridine (5 mL). The reaction mixture was stirred at 40° C. for 48 h. The reaction mixture was filtered and the filtrate concentrated in vacuo. Purification was carried out using flash column chromatography eluting the column (ISOLUTE SI) with a gradient of 0→5% CH$_3$OH in CHCl$_3$. The fractions with R$_f$=0.31 (10% CH$_3$OH/CHCl$_3$) afforded the title compound as a white crystalline solid (0.386 g, 37%).

$^1$H NMR (300 MHz, CDCl$_3$) δ 2.03 (2H, m, 2'-CHH and 5'-NH), 2.21 (1H, m, 5'-CHH), 2.37 (1H, m, 2'-CHH), 2.58 (1H, m, 5'-CHH), 3.31 (1H, bs, 3'-OH), 4.10 (1H, m, 4'-H), 4.24 (1H, m, 3'-H), 5.63 (1H, d, J=8.1 Hz, 5-H), 6.24 (1H, t,

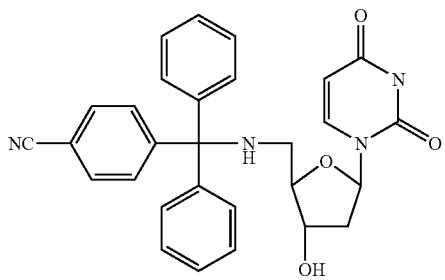

J=6.3 Hz, 1'-H), 7.00 (1H, dd, J=2.1, 8.1 Hz, 6-H), 7.18-7.48 (10H, m, Ph-H), 7.54 (2H, d, J=8.1 Hz, Ar—H), 7.66 (2H, d, J=8.1 Hz, Ar—H), 9.74 (1H, bs, 3-NH).

$^{13}$C NMR (75 MHz, CDCl$_3$) δ 40.7 (2'-CH$_2$), 46.5 (5'-CH$_2$), 71.3 (ArPh$_2$C), 72.8 (3'-CH), 85.6 (1'-CH), 86.5 (4'-CH), 103.3 (5-CH), 110.7 (Ar—CH), 119.2 (CN), 127.6 (Ph-CH), 128.7 (Ph-CH), 128.9 (Ph-CH), 129.1 (Ph-CH), 129.5 (Ar—CH), 132.4 (Ar—CH), 139.9 (6-CH), 144.3 (Ph-C), 145.0 (Ph-C), 150.8 (2-C), 151.6 (Ar—C), 163.8 (4-C).

ES$^+$ m/z (%) 517 ([M+Na]$^+$, 19), 495 ([M+H]$^+$, 9), 517 (CNTr$^+$, 100).

ES$^-$ m/z (%) 493 (M–H$^+$, 19), 111 (uracil-H$^+$, 100).

HRMS (ES$^+$) Found [M+H]$^+$ 495.2023; C$_{29}$H$_{27}$N$_4$O$_4$$^+$ requires 495.2027.

M.p. 160-163° C.

IR (KBr) 3387, 3177, 3027, 2230 (CN), 1699, 1661, 1466, 1267, 1097, 1039 cm$^-$.

Anal calcd for C$_{29}$H$_{29}$N$_3$O$_5$, 0.98(%): HCl, 0.40H$_2$O. C, 64.80; H, 5.21; N, 10.42; Cl, 6.46. found: C, 64.69; H, 4.90; N, 10.28; Cl, 6.84.

Example 23

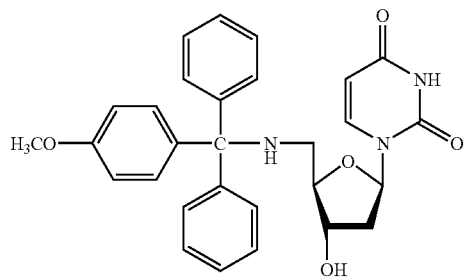

5'-paraMethoxytritylamino-2',5'-dideoxyuridine (23)

The procedure was similar to that described for example 20. 5'-Amino-2',5'-dideoxyuridine (0.204 g, 0.90 mmol) was reacted with 4-methoxytrityl (0.292 g, 0.99 mmol) to yield the title compound as a white solid (0.115 g, 26%).

$^1$H NMR (300 MHz, CDCl$_3$) δ 2.04 (2H, m, 2'-H), 2.29-2.48 (2H, m, 5'-H), 2.69 (1H, dd, J=3.7, 12.1 Hz, 5'—NH), 3.83 (3H, s, OCH$_3$), 4.15 (1H, m, 4'-H), 4.30 (1H, m, 3'-H), 5.69 (1H, d, J=8.1 Hz, 5-H), 6.32 (1H, t, J=6.4 Hz, 1'-H), 6.88 (2H, m, Ar—H), 7.17 (1H, d, J=8.1 Hz, 6-H), 7.21-7.61 (12H, m, Ar—H).

$^{13}$C NMR (75 MHz, CDCl$_3$) δ 40.8 (2'-CH$_2$), 46.6 (5'-CH$_2$), 55.7 (OCH$_3$), 70.7 (Ar$_3$C), 73.0 (3'-CH), 85.4 (4'-CH), 86.8 (1'-CH), 103.2 (5-CH), 113.7 (Ar—CH), 126.9 (Ar—CH), 128.4 (Ar—CH), 128.9 (Ar—CH), 1302 (Ar—CH), 138.0 (Ar—C), 139.9 (6-CH), 146.2 (Ar—C), 150.8 (2-C), 158.4 (Ar—C), 163.8 (4-C).

ES$^+$ m/z (%) 522 ([M+Na]$^+$, 27).

HRMS (ES$^+$) Found [M+H]$^+$ 500.2174; C$_{29}$H$_{30}$N$_3$O$_5$$^+$ requires 500.2180.

IR (KBr) 3052, 1713, 1694, 1682, 1666, 1650, 1506, 1250, 1034, 760 cm$^-$.

M.p. 140-142° C.

TLC (10% CH$_3$OH/CHCl$_3$) R$_f$=0.29.

Anal (%) found C, 65.69; H, 5.52; N, 7.86; Cl, 6.05. Calcd for C$_{29}$H$_{29}$N$_3$O$_5$, 0.87 HCl C, 65.56; H, 5.67; N, 7.91; Cl, 5.81.

Example 24

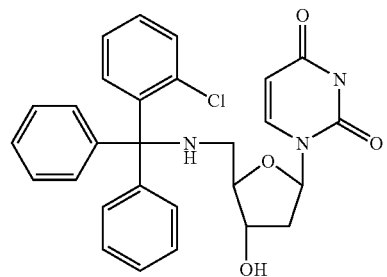

5'-[(2-chlorotrityl)amino]2',5'-dideoxyuridine (24)

5'-Amino-2',5'-dideoxyuridine (0.237 g, 1.04 mmol) was reacted with 2-chlorotrityl chloride (0.415 g, 1.33 mmol) in dry pyridine (5 mL) at 40° C. for 24 h. A second portion of 2-chlorotrityl chloride (0.198 g, 0.63 mmol) was added. After a further 2 h stirring at 40° C., the reaction was quenched with MeOH (2 mL). The reaction mixture was concentrated in vacuo and purified by flash column chromatography using an ISOLUTE Si column eluted with a gradient of 0→5% CH$_3$OH in CHCl$_3$. The fractions with R$_f$=0.17 (10% CH$_3$OH/CHCl$_3$) yielded the title compound as a white solid (85 mg, 16%).

$^1$H NMR (300 MHz, CDCl$_3$) δ 2.02 (1H, m, 2'-H), 2.20 (1H, m, 5'-H), 2.37 (1H, m, 2'-H), 2.53 (1H, m, 5'-H), 4.16 (1H, m, 3'-H), 4.24 (1H, m, 4'-H), 5.62 (1H, d, J=8.1 Hz, 5-H), 6.26 (1H, t, J=6.4 Hz, 1'-H), 7.05-7.45 (15H, m, 6-H and Ar—H).

$^{13}$C NMR (75 MHz, CDCl$_3$) δ 41.1 (2'-CH$_2$), 47.3 (5'-CH$_2$), 71.5 (ArPh$_2$C), 72.9 (3'-CH), 85.5 (1'-CH), 86.8 (4'-CH), 103.0 (5-CH), 126.8 (ClTr-CH), 126.9 (ClTr-CH), 127.6 (ClTr-CH), 128.4 (ClTr-CH), 128.5 (ClTr-CH), 128.6 (ClTr-CH), 129.2 (ClTr-CH), 132.3 (ClTr-CH), 132.9 (ClTr-CH), 134.7 (ClTr-C), 140.0 (6-CH), 140.9 (ClTr-C), 144.8 (ClTr-C), 146.0 (ClTr-C), 150.7 (2-C), 163.7 (4-C).

ES$^+$ m/z (%) 526 ([M+Na]$^+$, 11), 504 ([M+H]$^+$, 14), 277 (ClTr$^+$, 100).

ES$^-$ m/z (%) 504 (M–H$^+$, 11), 111 (uracil-H$^+$, 100).

HRMS (ES$^+$) Found [M+H]$^+$ 504.1689; C$_{28}$H$_{27}$N$_3$O$_4$Cl$^+$ requires 504.1685.

M.p. 129-131° C.

Example 25

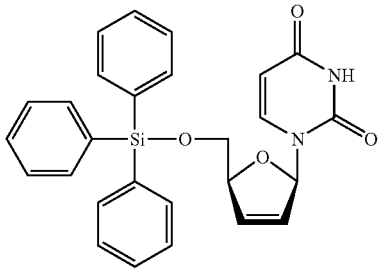

5'-Triphenylsilyloxy-2',3'-dideoxydidehydrouridine (25)

To a solution of 2',3'-dideoxydidehydrouridine (0.316 g, 1.50 mmol) in dry pyridine (5 mL) cooled in an ice-salt bath was added drop-wise a solution of triphenylsilyl chloride (0.595 g, 2.02 mmol) in dry pyridine (3 mL). The reaction mixture was kept at 0° C. under nitrogen for 2 h 30. As TLC monitoring evidenced the presence of unreacted starting material, additional triphenylsilyl chloride (0.296 g, 1.00 mmol) in dry pyridine (1 mL) was added. After 1 h 30 min the reaction was quenched with $CH_3OH$ (50 uL). Removal of the solvent in vacuo afforded a crude white gum which was purified by silica gel chromatography (Jones Chromatography Isolute SI column) eluted with 0→5% $CH_3OH$ in $CHCl_3$. The title was obtained as a white solid (0.476 g, 68%) from the fractions with $R_f$=0.57 (10% $CH_3OH/CHCl_3$).

$^1$H NMR (300 MHz, $CDCl_3$) δ 4.04 (1H, dd, J=2.2, 11.7 Hz, 5'-H), 4.19 (1H, dd, J=2.5, 11.7 Hz, 5'-H), 4.78 (1H, dd, J=1.9, 8.1 Hz, 5-H), 4.98 (1H, m, 4'-H), 5.90 (1H, d, J=5.7 Hz, 1'-H), 6.33 (1H, dd, J=1.4, 4.5 Hz, 2'-H), 7.12 (1H, m, 3'-H), 7.40-7.65 (15H, m, Ph-H), 7.80 (1H, d, J=8.1 Hz, 6-H), 8.99 (1H, bs, 3-NH).

$^{13}$C NMR (75 MHz, $CDCl_3$) δ 64.7 (5'-$CH_2$), 87.4 (1'-CH), 90.0 (4'-CH), 1026 (5-CH), 127.1 (2'-CH), 128.6 (Ph-CH), 131.0 (Ph-CH), 133.3 (Ph-C), 134.9 (3'-CH), 135.8 (Ph-CH), 141.5 (6-CH), 151.2 (2-C), 163.6 (4-C).

ES$^+$ m/z (%) 491 ([M+Na]$^+$, 36), 119 (100).

HRMS (ES$^+$) Found [M+NH$_4$]$^+$ 446.1887; $C_{25}H_{28}N_3OSi^+$ requires 446.1894.

M.p. 73-74° C.

Anal (%) found C, 67.75; H, 5.04; N, 5.84; Cl, 11.89. Calcd for $C_{27}H_{27}N_2O_4Si$, 0.25 HCl C, 67.89; H, 5.12; N, 5.86; Cl, 1.86.

Example 26

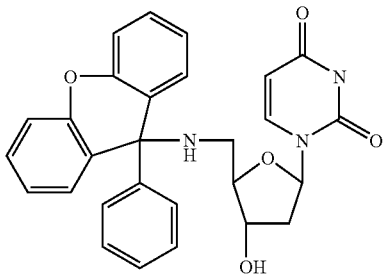

5'-Pixylamino-2',5'-dideoxyuridine (26)

2'-Amino-2',5'-deoxyuridine (0.231 g, 1.02 mmol) was reacted with pixyl chloride (0.390 g, 1.33 mmol) in dry pyridine (5 mL) at 40° C. for 48 h. $H_2O$ (10 mL) was added and the crude mixture was extracted with DCM (2×15 mL). The organic layers were dried over $Na_2SO_4$, concentrated in vacuo and purified by flash column chromatography eluting the column (ISOLUTE SI) with a gradient of 0→10% $CH_3OH$ in $CHCl_3$. The fractions with $R_f$=0.11 (10% $CH_3OH/CHCl_3$) yielded the title compound as a white solid (0.118 g, 24%).

$^1$H NMR (300 MHz, $CDCl_3$) δ 1.31 (1H, m, 2'-CHH), 2.04 (1H, m, 2'-CHH), 2.29 (1H, dd, J=4.3, 13.8 Hz, 5'-CHH), 2.58 (1H, m, 5'-CHH), 3.84 (2H, m, 3'-H and 4'-H), 5.69 (1H, d, J=8.1 Hz, 5-H), 6.21 (1H, t, J=6.5 Hz, 1'-H), 7.03-7.53 (14H, m, 6-H and Ar—H).

$^{13}$C NMR (75 MHz, $CDCl_3$) δ 39.4 (2'-$CH_2$), 42.3 (5'-$CH_2$), 72.1 (3'-CH), 76.9 (pixyl-C), 84.7 (1'-CH), 86.1 (4'-CH), 103.1 (5-CH), 116.8 (pixyl-CH), 116.9 (pixyl-CH), 123.3 (pixyl-C), 123.6 (pixyl-C), 123.97 (pixyl-CH), 124.03 (pixyl-CH), 127.4 (pixyl-CH), 127.6 (—CH), 128.2 (pixyl-CH), 130.20 (pixyl-CH), 130.24 (pixyl-CH), 131.1 (pixyl-CH), 131.5 (pixyl-CH), 140.3 (6-CH), 148.0 (pixyl-C), 150.5 (2-C), 151.4 (pixyl-C), 151.9 (pixyl-C), 163.5 (4-C).

ES$^+$ m/z (%) 506 ([M+Na]$^+$, 4), 257 (Pixyl$^+$ that is $C_{19}H_{13}O^+$, 100).

ES$^-$ m/z (%) 482 (M−H$^+$, 100).

HRMS (ES$^+$) Found [M+H]$^+$ 484.1871; $C_{28}H_{26}N_3O_5^+$ requires 484.1867.

M.p. 117-119° C.

Anal calcd for $C_{28}H_{25}N_3O_5$(%): 1.58 HCl C, 62.15; H, 4.95; N, 7.77. found C, 62.07; H, 4.66; N, 7.50.

Example 27

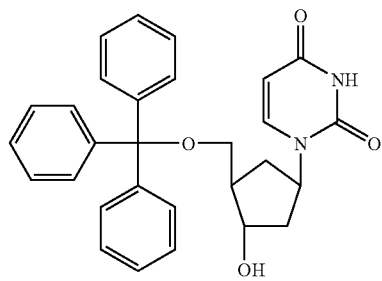

5'-O-trityl-2'-deoxyuridine (27)

2'-deoxyuridine (4.00 g, 17.5 mmol) and triphenylmethyl chloride (5.37 g, 19.25 mmol) were stirred in anhydrous pyridine (70 ml) at 50° C. overnight. Additional triphenylmethyl chloride (1.00 g, 3.59 mmol) was added after 18 hours, and the mixture was stirred for a further 4 hours at 50° C. The reaction mixture was then poured into ice-$H_2O$ (300 ml) and stirred vigorously. The precipitate was extracted with EtOAc (3×100 ml). The organic solution was then washed with 0.5 M HCl (4×100 ml), dried with $MgSO_4$ and filtered. The filtrate was then washed further with EtOAc, which was then evaporated, and finally with DCM. Solvent was removed using a Buchi rotary evaporator, and finally with the vacuum pump.

White solid (7.69 g, 93%).

Example 28

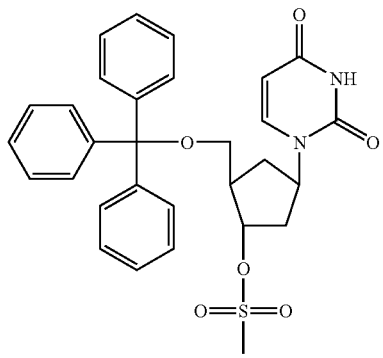

3'-O-Mesyl-5'-O trityl-2'-deoxyuridine (28)

Methanesulphonyl chloride (0.173 ml, 2.24 mmol) was added to a solution of (8) (0.30 g, 0.64 mmol) in anhydrous pyridine (5 ml) with ice-bath cooling. The mixture was stirred for 4 hours at room temperature. After this time, ice-water (1 ml) was added; the mixture was stirred for 5 minutes, then poured into ice-water (30 ml) and filtered. The precipitate was dissolved in CHCl$_3$ (30 ml), the solution was washed with 0.5 M HCl (10 ml) and water (3×10 ml), dried (MgSO$_4$), filtered, and reduced in vacuo which gave the title product as a yellow/orange solid (0.29 g, 83%).

Example 29

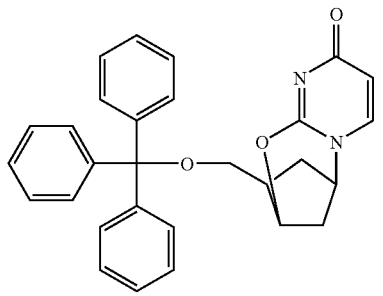

2,3'-Anhydro-5'-O-trityl-2',3-dideoxyuridine (29)

DBU (1.00 ml, 7.12 mmol) and compound 28 (3.55 g, 6.48 mmol) were stirred in DCM (25 ml) over 30 hours. The mixture was washed with water (2×30 ml), the organic layer was dried (MgSO$_4$), filtered and reduced in vacuo. The residue was purified by column chromatography (5% MeOH/CHCl$_3$) which gave the title product as a white solid (2.42 g, 82%).

Example 30

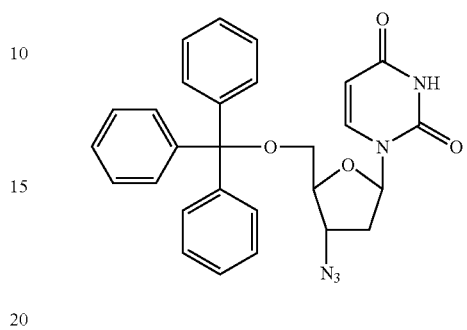

3'-Azido-5'-O-trityl-2',3'-dideoxyuridine (30)

Lithium fluoride (0.145 g, 5.61 mmol) was suspended in DMF (3 ml) and heated to 105° C. with stirring. To the stirred suspension was added N,N,N',N'-tetramethylethylenediamine (5 ml) followed by azidotrimethylsilane (0.64 g, 5.61 mmol). After stirring for an hour, compound 29 (1.41 g, 3.11 mmol) dissolved in N,N-dimethylformamide (2 ml) was added, and the reaction was allowed to proceed for 20 hours at 110° C. The mixture was cooled, poured into CHCl$_3$ (110 ml) and filtered through Celite. The solvent was removed under reduced pressure and the residue (brown oil) was taken in EtOAc (100 ml). The organic phase was washed with water (4×180 ml), dried (MgSO$_4$), filtered and concentrated. The concentrated mixture was purified by column chromatography (3% MeOH/CHCl$_3$) which gave the title product as an orange solid (0.996 g, 65%).

Example 31

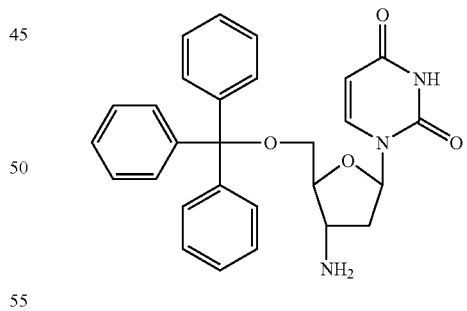

3'-Amino-5'-O-trityl-2',3'-dideoxyuridine (31)

Lidlar's catalyst (20 mg) was added to compound 30 (0.10 g, 0.20 mmol), and was then suspended in ethanol (5 ml). Air was removed from the flask by flushing with nitrogen several times. The nitrogen was then removed and replaced with hydrogen. The mixture was stirred for 5 hours, and then filtered through Celite. Fresh Lidlar's catalyst (20 mg) was added to the filtrate. The flask was flushed with nitrogen and then hydrogen as previously, and the reaction was left stirring for another 3 hours. The reaction mixture was filtered through Celite. The solvent was evaporated and the concentrated solution was purified by column chromatography (MeOH/DCM 2%→10%) which gave the title product as a white solid (0.065 g, 70%). $R_f$: 0.3 in DCM/MeOH 90:10.

$^1$H-NMR (300 MHz, CDCl$_3$): δ 7.97 (d, J=8.2 Hz, 1H, H-6), 7.47-7.27 (m, 15H, H-aromatic), 6.20 (q, J=3.3 Hz, 1H, H-1') 5.41 (d, J=8.1 Hz, 1H, H-5), 3.73-3.38 (m, 5H, H-3', H-4', H-5'), 2.44-2.18 (m, 2H, H-2').

$^{13}$C-NMR (75 MHz, CDCl$_3$): δ 163.5 (C-4). 150.5 (C-2), 143.7 (C-7'), 140.7 (C-6), 129.1 (C-8'), 128.5 (C-9'), 127.8 (C-10'), 102.2 (C-5), 87.9 (C-6'), 87.2 (C-4'), 85.2 (C-1'), 62.2 (C-5'), 50.7 (C-3'), 42.7 (C-2').

LRMS: (ES+ mode): m/z=491.7 [(M+Na)$^+$, 45%]; m/z=243.2 [(Tr)$^+$, 100%].

HRMS: (ES+ mode): found 492.1902; required 492.1899 for $C_{28}H_{27}N_3O_4Na$ [M Na]$^+$.

Microanalysis calculated for $C_{28}H_{27}N_3O_4\times0.5H_2O$: C, 70.28; H, 5.90; N, 8.78%. found: C, 70.64; H, 5.92; N, 8.41%.

Example 32

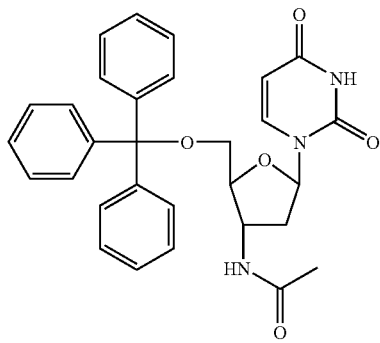

3'-Acetylamino-5'-O-trityl-2',3'-dideoxyuridine (32)

Compound 31 (0.10 g, 0.213 mmol) was suspended in DCM (5 ml), and to this was added acetic anhydride (0.047 g, 0.044 ml, 0.469 mmol) and triethylamine (0.065 ml, 0.469 mmol). The mixture was stirred at room temperature for 3 hours. After this time the solvent was evaporated to give a white solid. The product was purified by column chromatography (MeOH/DCM 2%→6%), and evaporation of the solvent gave the title compound as a white solid (0.103 g, 95%).

$R_f$: 0.45 in DCM/MeOH 90:10.

$^1$H-NMR (300 MHz, CDCl$_3$): δ 9.82 (s, 1H, N—H), 7.83 (d, J=8.2 Hz, 1H, H-6), 7.46-7.28 (m, 16H, H-aromatic) 6.94 (s, 1H, N—H), 6.34 (t, J=6.3 Hz, 1H, H-1'), 5.39 (d, J=8.1 Hz, 1H, H-5), 4.79-4.72 (m, 1H, H-3'), 4.07 (s, 1H, H-4') 3.59-3.47 (m, 2H, H-5'), 2.50-2.32 (m, 2H, H-2'), 2.04 (s, 3H, H-12')

$^{13}$C-NMR (75 MHz, CDCl$_3$): δ 163.6 (C-4), 154.9 (C-2), 143.6 (C-7'), 140.5 (C-6), 129.1 (C-8'), 128.5 (C-9'), 127.9 (C-10'), 103.1 (C-5), 88.1 (C-6'), 87.3 (C-1'), 85.2 (CH, C-4'), 62.1 (C-5'), 50.9 (C-3'), 38.8 (C-2')

LRMS: (ES+ mode): m/z=533.8 [(M+Na)$^+$, 20%].

HRMS: (ES+ mode): Found 534.2009; required 534.2005 for $C_{30}H_{29}N_3O_5Na$ [M+Na]$^+$ Microanalysis calculated for $C_{30}H_{29}N_3O_5\times1.0$ HCl$\times$ 1.0H$_2$O C, 63.66; H, 5.70; N, 7.42%. found C, 63.20; H, 5.15; N, 7.11%.

Example 33

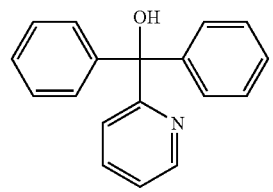

Diphenyl(pyridin-2-yl)methanol (33)

A solution of 2-bromopyridine (5 g, 0.032 mol) in dry THF (150 mL) was cooled to −70° C. To this cooled solution was added n-BuLi (2.8 M, 12.4 mL, 0.034 mol) over a period of 20 min and allowed to stir for 2 h under N$_2$ atmosphere. A solution of benzophenone (5.8 g, 0.032 mol) in dry THF (50 mL) was added to the solution at the same temperature over a period of 30 min. The reaction mixture was warmed slowly to RT and allowed to stir another 5 h at RT. The reaction mixture was concentrated under vacuum and the residue was washed with petroleum ether. The organic layer was filtered and the filtrate was concentrated under vacuum to give the title compound (8 g, 95%).

Example 34

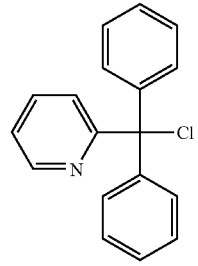

2-[Chloro(diphenyl)methyl]pyridine hydrochloride (34)

To a mixture of diphenyl(pyridin-2-yl)methanol (4 g, 0.015 mol) in thionylchloride (50 mL) was added acetylchloride (15 mL, 0.195 mol) at RT and heated to 50° C. for 48 h. The reaction mixture was concentrated under vacuum and the residue was azeotroped with dry benzene (100 mL×2) to give the title compound as the hydrochloride salt (4.4 g, >95%).

Example 35

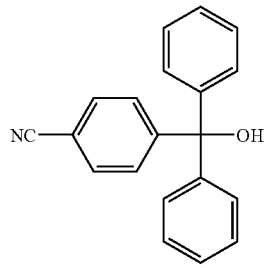

4-[Hydroxy(diphenyl)methyl]benzonitrile (35)

The procedure described in example 49 was followed but using 4-bromobenzonitrile (5 g, 0.027 mol) instead of 2-bromopyridine which gave the title compound (7.5 g, 94%).

Example 36

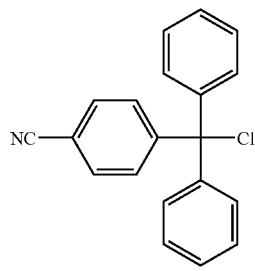

4-[Chloro(diphenyl)methyl]benzonitrile (36)

To a mixture of 4-[hydroxy(diphenyl)methyl] in dry toluene (60 mL) was added acetylchloride (3 mL) at RT and heated to 50° C. for 12 h. The reaction mixture was concentrated under vacuum. The residue was recrystallized from pet ether to give the product (1.7 g, 40%).

Example 37

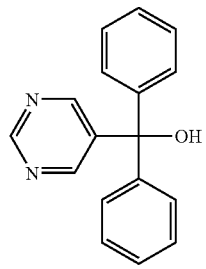

Diphenyl(pyrimidin-5-yl)methanol (37)

A solution of 5-bromopyrimidine (10 g, 0.063 mol) in a mixture of dry THF (150 mL) and hexane (50 mL) was cooled to −100° C. To this cooled solution was added n-BuLi (4 g, 21 mL, 0.062 mol) over a period of 30 min and stirred for another 30 min. A solution of benzophenone (11.5 g, 0.063 mol) in dry THF (50 mL) was added to this at the same temperature over a period of 30 min. The reaction mixture was warmed slowly to RT and allowed to stir another 1 h at RT. The reaction was quenched with cold water (200 mL), ethyl acetate was added and the organic layer was separated. The organic layer was dried, concentrated and the crude product was purified by column chromatography on silica gel (up-to 25% ethyl acetate in pet ether) to give the product (8 g). TLC: Pet. ether/EtOAc, 1:1, $R_f$=0.3.

Example 38

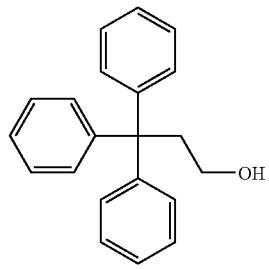

2,2,2-Triphenylethanol (38)

To a suspension of LAH (3.9 g, 0.104 mol) in dry THF (200 mL) was stirred at 0° C. for 20 min. A solution of 2,2,2-triphenylacetic acid (10 g, 0.034 mol) in dry THF (50 mL) was added in a drop-wise manner. The reaction mixture was stirred at RT overnight. Excess LAH was quenched with 1.5 N HCl and the reaction mixture was further stirred for 2 h at RT. The reaction mixture was filtered through celite, washed with ethyl acetate and the filtrate was concentrated under vacuum. The crude product was purified by column chromatography on silica gel (4% ethyl acetate in pet ether) to give the title compound (4.6 g, 48%). TLC: Pet. ether/EtOAc, 7:3, $R_f$=0.2

Example 39

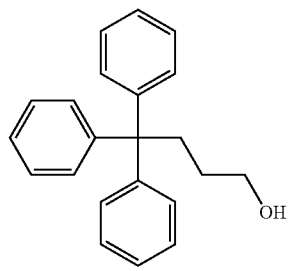

3,3,3-Triphenylpropan-1-ol (39)

To a magnetically stirred suspension of LAH (8.3 g, 0.219 mol) in dry THF (50 mL) was added a solution of 3,3,3-triphenylpropionic acid (9.5 g, 0.0314 mol) over a period of 30 min at 0° C. The reaction mixture was allowed to stir at RT for 14 h. The reaction mixture was cooled and excess LAH was quenched with 20% NaOH solution (50 mL). The reaction mixture was passed through celite, washed with THF and the filtrate was concentrated under vacuum. The residue was washed with pet ether and dried which gave the title compound (8 g, >85%).

TLC: Pet. ether/EtOAc, 7:3, $R_f$=0.2

Example 40

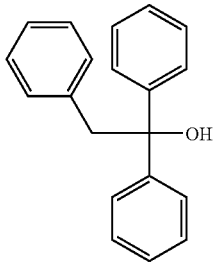

1,1,2-Triphenylethanol (40)

To a suspension of Mg (1.7 g, 0.07 mol) in dry ether (25 mL) was added a solution of benzyl bromide (10 mL, 1.5 equ.) in dry ether (25 mL) drop-wise and allowed to stir at RT for 1 h. By the time all magnesium was dissolved and the reaction mixture was cooled to 0° C. To this was added a solution of benzophenone (10 g, 0.05 mol) in dry ether (25 mL) and allowed to stir at RT for 5 h. The progress of the reaction was followed by TLC and when it was ready the reaction mixture was quenched with saturated NH$_4$Cl solution, extracted with ether (100 mL), washed with brine, dried and concentrated under vacuum. The crude product was purified by column chromatography on silica gel (10% ethyl acetate in pet. ether) to give the title compound (9.6 g, 65%) as a white solid.

TLC: Pet. ether/EtOAc, 9:1, $R_f$=0.4

Example 41

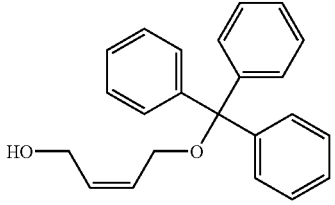

4-Trityloxy-but-2-en-1-ol (41)

Trityl chloride (557 mg; 2 mmol) Et$_3$N (0.306 ml; 2.2 mmol) and DMAP (10 mg; 0.08 mmol) were added to a emulsion of cis-2-buten-1,4-diol (1.76 g; 20 mmol) in DCM (10 ml). The mixture was stirred at room temperature under atmosphere of nitrogen for 24 hours. After such period of time the complete disappearance of trityl chloride was observed by TLC (EtOAc/Hexane 50:50). DCM (20 ml) and water (10 ml) were added to the mixture. The phases were separated and the organic layer was washed with water (10 ml) and brine (10 ml). The solvent was dried over MgSO$_4$ and evaporated under reduced pressure affording a residue (white oil) which was purified by flash chromatography using Hexane/EtOAc 70:30→40:60 as gradient which gave the title product as a colourless oil (563 mg, 81%).

Example 42

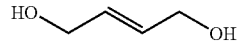

Trans-2-buten-1,4-diol (42)

2-Butyn-1,4-diol (1 g; 11.64 mmol) was dissolved in dry THF (25 ml) under atmosphere of nitrogen. The solution was cooled to −78° C. with a dry-ice/acetone bath. A cold solution of LAH in THF 1M (12.7 ml; 12.7 mmol) was added with a syringe. The reaction was left worm to room temperature in 4 hours. The disappearance of the starting alkyne was observed by TLC (Hexane/EtOAc 30:70); then the solution was cooled to −0° C. with an ice bath and the quenched with NaOH 1M, until no gas was developed. The pH was adjusted to 8 with HCl 1M and then silica was added to the solution. The solvents were removed under reduced pressure and the residue was loaded into a chromatographic column and purified using Hexane/EtOAc 30:70 as eluent which gave the title compound as a colourless oil (817 mg, 79%). $R_f$: 0.11 in Hexane/EtOAc 30:70 (PMA).

$^1$H-NMR (300 MHz, CD$_3$OD): δ 5.83 (bs; 2H; H-2+H-3); 4.07 (d; J=3.57 Hz; 4H; H-1+H-4)

$^{13}$C-NMR (75 MHz, CD$_3$OD): δ 131.7 (C-2 & C-3); 63.4 (C-1 & C-4)

LRMS (ES$^+$): m/z 111.0 [M+Na]$^+$ 100%.

Example 43

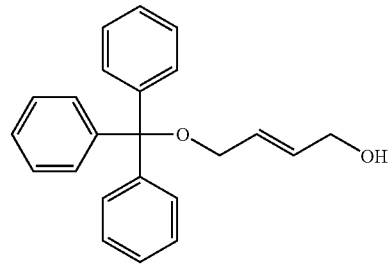

(E)-4-(Trityloxy)but-2-en-1-ol (43)

A solution of Trityl chloride (500 mg; 1.81 mmol), TEA (0.277 ml; 1.99 mmol) and DMAP (8.8 mg; 0.072 mmol) In dry DCM (5 ml) was added with a syringe to a solution of the diol (10) (800 mg; 9.07 mmol) in DCM (15 ml). The mixture was stirred at room temperature for 1 hour and 30 minutes, then other TrCl, TEA and DMAP (half quantities than before) were added. The reaction was stirred at the same temperature until TLC (Hexane/EtOAc 50:50) showed complete disappearance of Trityl chloride. After 1.5 hours water (20 ml) was added and the reaction was stirred for few minutes, then the phases were separated. The organic layer was washed with water (25 ml) and brine (25 ml). The solvent was dried over MgSO$_4$ and evaporated to afford a crude oil which was purified by flash chromatography using Hexane/EtOAc 50:50 as eluent which gave the title compound as a colourless oil, 637 mg, 71%. R$_f$: 0.72 in Hexane/EtOAc 50:50 (UV/PMA).

$^1$H-NMR (300 MHz, CDCl$_3$): δ 7.54-7.51 (m; 6H; H-7); 7.39-7.27 (m; 9H; H-8+H-9); 6.12-6.03 (m; 1H; H-3); 5.91-5.83 (m; 1H; H-2); 4.24 (bs; 2H; H-4); 3.71-3.71 (m; 2H; H-1).

$^{13}$C-NMR (75 MHz, CDCl$_3$): δ 144.6 (C-6); 130.5 (C-3 & C-2); 129.0 (C-8); 128.7 (C-7); 127.4 (C-9); 87.3 (C-5); 64.5 (C-4); 63.8 (C-1).

LRMS (ES+): m/z 331.2 [M+H]$^+$ 100%.

Example 44

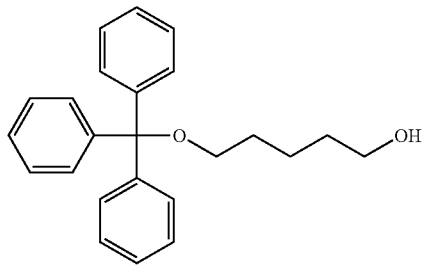

5-Trityloxypentanol (44)

The procedure described in example 41 was followed but using 1,5-pentandiol (376 mg, 3.6 mmol) as alcohol instead of cis-2-buten-1,4-diol in the reaction with trityl chloride, which gave the title compound (300 mg, 24%).

Example 45

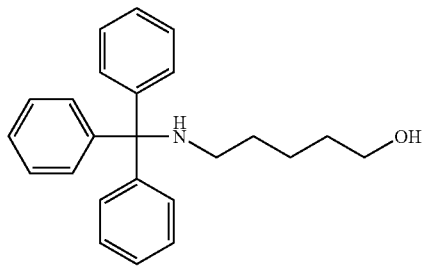

5-(Tritylamino)-pentan-1-ol (45)

The title compound (24%) was prepared as described in example 41 but using 5-aminopentanol instead of cis-2-buten-1,4-diol in the reaction with trityl chloride.

BIOLOGICAL EXAMPLES

Example B1

Malaria Whole Cell Assays

Parasite Cultures

Two strains of *P. falcipanum* are used in this study: The drug sensitive NF54 (an airport strain of unknown origin) and K1 (Thailand, chloroquine and pyrimethamine resistant). The strains are maintained in RPMI-1640 medium with 0.36 mM hypoxanthine supplemented with 25 mM HEPES, 25 mM NaHCO$_3$, neomycin (100 U/ml) and Albumax® (lipid-rich bovine serum albumin) (GIBCO, Grand Island, N.Y.) (5 g/l), together with 5% washed human A+ erythrocytes. All cultures and assays are conducted at 37° C. under an atmosphere of 4% CO$_2$, 3% O$_2$ and 93% N$_2$. Cultures are kept in incubation chambers filled with the gas mixture. Subcultures are diluted to a parasitaemia of 0.1-0.5% and the medium changed daily.

Drug Sensitivity Assays

Antimalarial activity is assessed using an adaptation of the procedures described by Desjardins et al. (Antimicrob. Agents Chemother. 16(6):710-8, 1979), and Matile and Pink (In: Lefkovits, I. and Pernis, B. (Eds.). Immunological Methods. Academic Press, San Diego, pp. 221-234, 1990).

Stock drug solutions are prepared in 100% DMSO (dimethylsulfoxide) at 10 mg/ml, unless otherwise suggested by the supplier, and heated or sonicated if necessary. After use the stocks are kept at −20° C. The compound is further diluted to the appropriate concentration using complete medium without hypoxanthine.

Assays are performed in sterile 96-well microtiter plates, each well containing 200 μl of parasite culture (0.15% parasitemia, 2.5% hematocrit) with or without serial drug solutions. Seven 2-fold dilutions are used covering a range from 5 μg/ml to 0.078 μg/ml.

For active compounds the highest concentration is lowered (e.g. to 100 ng/ml), for plant extracts the highest concentration is increased to 50 μg/ml. Each drug is tested in duplicate and repeated once for active compounds showing an IC$_{50}$ below 0.5 μg/ml. After 48 hours of incubation at 37° C., 0.5 μCi $^3$H-hypoxanthine is added to each well. Cultures are incubated for a further 24 h before they are harvested onto glass-fiber filters and washed with distilled water. The radioactivity is counted using a Betaplate™ liquid scintillation counter (Wallac, Zurich, Switzerland). The results are recorded as counts per minute (CPM) per well at each drug concentration and expressed as percentage of the untreated controls. From the sigmoidal inhibition curves IC$_{50}$ values are calculated.

Primary Screen

K1 strain is used. The compounds are tested at 7 concentrations (5000 to 78 ng/ml). Artemisinin and chloroquine are included as reference drugs.

If the IC$_{50}$ is >5 μg/ml, the compound is classified as inactive

If the IC$_{50}$ is 0.5-5 μg/ml, the compound is classified as moderately active If the IC$_{50}$ is <0.5 μg/ml, the compound is classified as active and is further evaluated using two strains, K1 and NF54. A new range of concentrations is chosen depending on the IC$_{50}$ determined (e.g. 100 to 1.56 ng/ml) and the assay is carried out 2× independently.

The standard drugs are chloroquine and artemisinin which are run in the same assay. The IC$_{50}$ values for chloroquine are 2.9 ng/ml for NF54 and 48 ng/ml for K1; for artemisinin 1.9 ng/ml for NF54 and 0.8 ng/ml for K1.

Secondary Screen

Test compounds are tested against a panel of say, 14 different of different origin and some show resistances to chloroquine and/or pyrimethamine. If the range of the IC$_{50}$ values for the 14 strains is within a factor 3-5× then the tested compound is considered not to show cross resistance.

Example B2

Malaria Enzyme Assays

Inhibition of *Plasmodium falciparum* dUTPase

Chemicals

2'-dUTP, was purchased from Pharmacia. $MgCl_2$, BSA, and the pH indicator cresol red were from Sigma. The buffer N,N-bis(2-hydroxyethyl)glycine (BICINE) was obtained from USB (United States Biochemical), Ohio. All the concentrations of nucleotides were calculated spectrophotometrically (HP-8453, Hewlett Packard) at 280 nm, using the extinction coefficient ($\epsilon_{280\ nm}$=1.75 ml $mg^{-1}cm^{-1}$). Other chemicals used in these experiments were of the highest quality available.

Cloning of the PFdut Gene

Conserved motifs of the human dUTPase enzyme were used as query to identify the PFdut gene in the www.tigr.org database of the *Plasmodium falciparum* 3D7 strain. The entire coding sequence was amplified by the PCR using as template cDNA and as primers the oligonucleotides ATG-PFdut (CATATGCATTTAAAAATTGTATGTCTG) and TGA-PFdut (GGATCCTCAATATTTATTATCGATGTC-GATC) which were designed so that NdeI and BamHI restriction sites were introduced at the 5 and 3 ends for convenient cloning in the expression vector pET11 (Stratagene). The amplified product was cloned into pGEMT (Promega) and propagated in *E. coli* XL1B cells. In order to confirm the correct sequence after amplification, sequencing was performed using an Applied Biosystems Automated Sequencer, at the Analytical Services of the Instituto de Parasitología y Biomedicina "López Neyra". These Services also supplied the oligonucleotides designed for the sequencing

*P. fialciparum* dUTPase Overexpression and Purification

Recombinant *P. falciparum* dUTPase was purified from *E. coli* BL21 (DE3) cells transformed with pET-PFdut. Pellets from a liter of culture were resuspended in a solution consisting of buffer A (20 mM MES pH 5.5, 50 mM NaCl, 1 mM DTT) plus the protease inhibitors 1 mM PMSF, 20 µg/ml leupeptin and 1 mM benzamidine. Purification was carried out in a cold room (4° C.). The soluble crude extract was obtained by sonication in a Vibra-cell (Sonics and Materials Inc. Danbury, Conn., USA) and centrifugation at 14000×g. The extract was loaded onto a phosphocellulose column (Whatman) pre-equilibrated with buffer A at a flow rate of 1 ml/min. After washing the column with 100 ml of buffer A, elution was performed using a linear NaCl gradient of 50 to 1000 mM. Peak fractions with a low concentration of contaminating protein, as judged by 15% SDS-PAGE gels, were pooled and then loaded and chromatographed on a Superdex 200 column at a flow rate of 0.5 ml/min. The column was equilibrated with buffer B (50 mM Bicine, 1 mM DTT, 10 mM $MgCl_2$). Peak fractions were pooled and concentrated to about 5 mg/ml by ultrafiltration in a Centripep tube (Amicon) and stored at −80° C.

Kinetic Measurements

Nucleotide hydrolysis was monitored by mixing enzyme and substrate with a rapid kinetic accessory (Hi-Tech Scientific) attached to a spectrophotometer (Cary 50) and connected to a computer for data acquisition and storage. Protons, released through the hydrolysis of nucleotides, were neutralised by a pH indicator in a weak buffered medium with similar $pK_a$ and monitored spectrophotometrically at the absorbance peak of the basic form of the indicator. Absorbance changes were kept within 0.1 units. The indicator/buffer pair used was cresol red/BICINE (2 mM/50 µM, pH 8, 573 nm). The measurements were performed at 25° C., and the solutions were previously degassed. Assays contained 30 nM purified recombinant enzyme, 50 µM dUTP, 5 mM $MgCl_2$ and 2.5 mM DTT, 1.25 mg/ml BSA and 100 mM KCl. Indicator absorbance changes corresponding to complete hydrolysis of nucleotides were recorded in the computer, and the kinetic parameters $V_{max}$ and $K_{mapp}$ (or slope) were calculated by fitting the data to the integrated Michaelis-Menten equation (Segel, 1975).

$$[dUMP]/t = V_{max} - K_{map}/t \ln [dUTP]([dUTP]-[dUMP])$$

Solutions of potential inhibitors were prepared at 10 mg/ml and tested routinely at concentrations of 2, 10, and 50 µg/µl. A wider range of concentrations was further tested when necessary for $K_i$ determination. The different apparent $K_m$ values attained were plotted against inhibitor concentration and $K_i$ values were obtained according to the following equation:

$$K_{map} = \frac{K_m}{K_i}[I] + K_m$$

Example B3

Human dUTPase Assay

Human recombinant dUTPase was purified from *E. coli* BL21 (DE3) cells transformed with pETHudut (Dr. P. O. Nyman, Lund University). Purification was accomplished as described for the dUTPase above except that the last step in Superdex 200 was omitted. Likewise, conditions for enzyme assays were the same as described above except that the enzyme concentration was 50 nM.

Example B4

*Trypanosoma brucei* Whole Cell Assays

Parasite Cultures

Three strains of *T. brucei* spp. are used in this study: (a) *Trypanosoma brucei rhodesiense* STIB 900, a clone of a population isolated in 1982 from a patient in Tanzania which is known to be susceptible to all currently used drugs; (b) *Trypanosoma brucei gambiense* STIB 930, a derivative of strain TH1/78E (031) isolated in 1978 from a patient in Ivory Coast which is known to be sensitive to all drugs used, and (c) *Trypanosoma brucei brucei* STIB 950, a clone of a population isolated in 1985 from a bovine in Somalia which shows drug resistance to diminazene, isometamidium and quinapyramine.

The bloodstream form trypomastigotes of the strains a and c are maintained in MEM medium with Earle's salts supplemented with 25 mM HEPES, 1 g/l additional glucose, 1% MEM nonessential amino acids (100×), 0.2 mM 2-mercaptoethanol, 2 mM Na-pyruvate, 0.1 mM hypoxanthine and 15% heat inactivated horse serum.

The bloodstream form trypomastigotes of strain b are maintained in MEM medium with Earle's salts supplemented with 25 mM HEPES, 1 g/l additional glucose, 1% MEM non-essential aminoacids (100×), 0.2 mM 2-mercaptoethanol, 2 mM Na-pyruvate, 0.1 mM hypoxanthine, 0.05 mM bathocuproine disulphonic acid, 0.15 mM L-cysteine and 15% heat inactivated pooled human serum.

All cultures and assays are conducted at 37° C. under an atmosphere of 5% $CO_2$ in air.

Drug Sensitivity Assays

Stock drug solutions are prepared in 100% DMSO (unless otherwise suggested by the supplier) at 10 mg/ml, and heated or sonicated if necessary. After use the stocks are kept at −20° C. For the assays, the compound is further diluted to the appropriate concentration using complete medium.

Assays are performed in 96-well microtiter plates, each well containing 100 µl of culture medium with $8\times10^3$ bloodstream forms with or without a serial drug dilution. The highest concentration for the test compounds is 90 µg/ml. Seven 3-fold dilutions are used covering a range from 90 µg/ml to 0.123 µg/ml. Each drug is tested in duplicate and each assay is repeated at least once. After 72 hrs of incubation the plates are inspected under an inverted microscope to assure growth of the controls and sterile conditions.

10 µl of Alamar Blue (12.5 mg resazurin dissolved in 100 ml distilled water) are now added to each well and the plates incubated for another 2 hours. Then the plates are read with a Spectramax Gemini XS microplate fluorometer (Molecular Devices Cooperation, Sunnyvale, Calif., USA) using an excitation wave length of 536 nm and an emission wave length of 588 nm. Data are analysed using the microplate reader software Softmax Pro (Molecular Devices Cooperation, Sunnyvale, Calif., USA).

Primary Screen

The preliminary screen uses the *Trypanosoma b. rhodesiense* strain. The compounds are tested at 7 concentrations (drug concentrations ranging from 90 µg/ml to 0.123 µg/ml in 3-fold dilutions).

If the $IC_{50}$ is >3 µg/ml, the compound is classified as inactive

If the $IC_{50}$ is 0.2-3 µg/ml, the compound is classified as moderately active If the $IC_{50}$ is <0.21 g/ml, the compound is classified as active The standard drug is melarsoprol which is run in the same assay; the ICo for melarsoprol is 1.6 ng/ml.

Secondary Screen

Active compounds ($IC_{50}$<0.2 µg/ml) are tested against the *Trypanosoma brucei gambiense* STIB 930 and the drug resistant *T. b. brucei* STIB 950 following the same protocol as described above.

The standard drug is melarsoprol which is run in the same assay; the $IC_{50}$ for melarsoprol is 4.2 ng/ml for STIB 930 and 2.8 ng/ml for STIB 950

Example B5

*Trypanosoma cruzi* Whole Cell Assays

*Trypanosoma cruzi* Cell Cultures:

The *Trypanosoma cruzi* Tulahuen C2C4 strain, containing the -galactosidase (Lac Z) gene, is used. The plasmid construct by Dr. S. Reed was obtained from Dr. F. Buckner, Seattle, as epimastigotes in LIT medium.

The infective amastigote and trypomastigote stages are cultivated in L-6 cells (rat skeletal myoblast cell line) in RPMI 1640 supplemented with 2 mM L-glutamine and 10% heat-activated foetal bovine serum in 12.5 $cm^2$ tissue culture flasks. Amastigotes develop intracellularly, differentiate into trypomastigotes and leave the host cell. These trypomastigotes infect new L-6 cells and are the stages used to initiate an infection in the assay. All cultures and assays are conducted at 37° C. under an atmosphere of 5% $CO_2$ in air.

Drug Sensitivity Assays

Stock drug solutions are prepared in 100% DMSO (dimethylsulfoxide) unless otherwise suggested by the supplier at 10 mg/ml, and heated or sonicated if necessary. The stocks are kept at −20° C. For the assays, the compound is further diluted to the appropriate concentration using complete medium.

Assays are performed in sterile 96-well microtiter plates, each well containing 100 µl medium with $2\times10^3$ L-6 cells. After 24 hours 50 µl of a trypanosome suspension containing $5\times10^3$ trypomastigote bloodstream forms from culture are added to the wells. 48 hours later the medium is removed from the wells and replaced by 100 µl fresh medium with or without a serial drug dilution. At this point the L-6 cells should be infected with amastigotes and no free trypomastigotes should be in the medium. Seven 3-fold dilutions are used covering a range from 90 µg/ml to 0.123 µg/ml. Each drug is tested in duplicate. After 96 hours of incubation the plates are inspected under an inverted microscope to assure growth of the controls and sterility.

Then the substrate CPRG/Nonidet (50 l) is added to all wells. A colour reaction will become visible within 2-6 hours and can be read photometrically at 540 nm. Data are transferred into a graphic programme (e.g. EXCEL), sigmoidal inhibition curves determined and $IC_{50}$ values calculated.

Primary Screen

Benznidazole is used as the reference drug and shows an $IC_{50}$ value of 0.34 µg/ml.

If the $IC_{50}$ is >30 µg/ml, the compound is classified as inactive.

If the $IC_{50}$ is between 2 and 30 µg/ml, the compound is classified as moderately active.

If the $IC_{50}$ is <2 µg/ml, the compound is classified as active.

Example B6

Leishmaniasis

Macrophage In Vitro Screening Model

Parasite and Cell Cultures

The *Leishmania donovani* strain MHOM/ET/67/L82 obtained from Dr. S. Croft, London) is used. The strain is maintained in the Syrian Golden hamster. Amastigotes are collected from the spleen of an infected hamster Amastigotes are grown in axenic culture at 37° C. in SM medium (Cunningham I., J. Protozool. 24, 325-329, 1977) at pH 5.4 supplemented with 10% heat-activated foetal bovine serum under an atmosphere of 5% $CO_2$ in air.

Primary peritoneal macrophages from NMRI mice are collected 1 day after a macrophage production stimulation with an i.p injection of 2 ml of a 2% potato starch suspension (FLUKA, Switzerland) All cultures and assays are done at 37° C. under an atmosphere of 5% $CO_2$ in air.

Drug Sensitivity Assays

Stock drug solutions are prepared in 100% DMSO (unless otherwise suggested by the supplier) at 10 mg/ml, and heated or sonicated if necessary. After use the stocks are kept at −20° C. For the assays, the compound is further diluted in serum-free culture medium and finally to the appropriate concentration in complete medium.

Assays are performed in sterile 16-well chamber slides (LabTek, Nalgene/Nunc Int.) To each well 100 µl of a murine macrophage suspension (4×10$^5$/ml) in RPMI 1640 (containing bicarbonate and HEPES) supplemented with 10% heat inactivated fetal bovine serum is added. After 24 hrs 100 µl of a suspension containing amastigotes (1.2×10$^6$1 ml) is added resulting in a 3:1 ratio of amastigotes/macrophages. The amastigotes are harvested from an axenic amastigote culture and suspended in RPMI/FBS. 24 hrs later, the medium containing free amastigotes is removed, washed 1× and replaced by fresh medium containing four 3-fold drug dilutions. In this way 4 compounds can be tested on one 16-well tissue culture slide. Untreated wells serve as controls. Parasite growth in the presence of the drug is compared to control wells. After 4 days of incubation the culture medium is removed and the slides fixed with methanol for 10 min followed by staining with a 10% Giemsa solution. Infected and non-infected macrophages are counted for the control cultures and the ones exposed to the serial drug dilutions. The infection rates are determined. The results are expressed as % reduction in parasite burden compared to control wells, and the $IC_{50}$ calculated by linear regression analysis.

Primary Screen

The compounds are tested in duplicate at 4 concentrations ranging from 9 to 0.3 µg/m.

If the IC50 is below 0.3 µg/ml then the range is changed to 1 to 0.03 µg/ml. Miltefosine is used as the reference drug and shows an $IC_{50}$ value of 0.325 µg/ml (0.22-0.42 µg/ml; n=4)

If the $IC_{50}$ is higher than 10 µg/ml, the compound is classified as inactive.

If the $IC_{50}$ is between 2 and 10 µg/ml, the compound is classified as moderately active.

If the $IC_{50}$ is <2 µg/ml, the compound is classified as active and is further evaluated in a secondary screening.

Drug Sensitivity Assays

Stock drug solutions are prepared in 100% DMSO (dimethylsulfoxide) unless otherwise suggested by the supplier at 10 mg/ml, and heated or sonicated if necessary. The stocks are kept at −20° C. For the assays, the compound is further diluted to the appropriate concentration using complete medium.

Assays are performed in sterile 96-well microtiter plates, each well containing 100 µl medium with 2×10$^3$ L-6 cells. After 24 hours 50 µl of a trypanosome suspension containing 5×10$^3$ trypomastigote bloodstream forms from culture are added to the wells. 48 hours later the medium is removed from the wells and replaced by 100 µl fresh medium with or without a serial drug dilution. At this point the L-6 cells should be infected with amastigotes and no free trypomastigotes should be in the medium. Seven 3-fold dilutions are used covering a range from 90 µg/ml to 0.123 µg/ml. Each drug is tested in duplicate. After 96 hours of incubation the plates are inspected under an inverted microscope to assure growth of the controls and sterility.

Then the substrate CPRG/Nonidet (50 1) is added to all wells. A colour reaction will become visible within 2-6 hours and can be read photometrically at 540 nm. Data are transferred into a graphic programme (e.g. EXCEL), sigmoidal inhibition curves determined and $IC_{50}$ values calculated.

Primary Screen

Benznidazole is used as the reference drug and shows an $IC_{50}$ value of 0.34 µg/ml.

If the $IC_{50}$ is >30 µg/ml, the compound is classified as inactive.

If the $IC_{50}$ is between 2 and 30 µg/ml, the compound is classified as moderately active.

If the $IC_{50}$ is <2 µg/ml, the compound is classified as active.

Example B7

*Leishmania donovani*

Axenic Amastigote Assay

Parasite and Cell Cultures:

The *Leishmania donovani* strain MHOM/ET/67/L82) is used. The strain is maintained in the hamster. Amastigotes are collected from the spleen of an infected hamster and adapted to axenic culture conditions at 37° C. The medium is a 1:1 mixture of SM medium (Cunningham I., J. Protozool. 24, 325-329, 1977) and SDM-79 medium (Brun, R. & Schönenberger, M., Acta Trop. 36, 289-292, 1979) at pH 5.4 supplemented with 10% heat-inactivated FBS under an atmosphere of 5% $CO_2$ in air.

Drug Sensitivity Assays

Stock drug solutions are prepared in 100% DMSO (unless otherwise suggested by the supplier) at 10 mg/ml, and heated or sonicated if necessary. After use the stocks are kept at −20° C. For the assays, the compound is further diluted to the appropriate concentration using complete medium.

Assays are performed in 96-well microtiter plates, each well containing 100 µl of culture medium with 10$^5$ amastigotes from axecic culture with or without a serial drug dilution. The highest concentration for the test compounds is 90 µg/ml. Seven 3-fold dilutions are used covering a range from 30 µg/ml to 0.041 µg/ml. Each drug is tested in duplicate and each assay is repeated at least once. After 72 hours of incubation the plates are inspected under an inverted microscope to assure growth of the controls and sterile conditions.

10 µl of Alamar Blue (12.5 mg resazurin dissolved in 1 L distilled water) are now added to each well and the plates incubated for another 2 hours. Then the plates are read with a Spectramax Gemini XS microplate fluorometer (Molecular Devices Cooperation, Sunnyvale, Calif., USA) using an excitation wave length of 536 nm and an emission wave length of 588 nm.

Data are analysed using the microplate reader software Softmax Pro (Molecular Devices Cooperation, Sunnyvale, Calif., USA).

Primary Screen

The compounds are tested in duplicate at 7 concentrations. Miltefosine is used as the reference drug and shows an $IC_{50}$ value of 0.12 µg/ml.

If the $IC_{50}$ is >3 µg/ml, the compound is classified as inactive

If the $IC_{50}$ is 0.1-3 µg/ml, the compound is classified as moderately active If the $IC_{50}$ is <0.1 µml, the compound is classified as active Secondary Screen Active and moderately active compounds are tested in the macrophage assay with intracellular amastigotes in their host cells, murine macrophages.

Example B8

Biological Results

Compounds of the invention, such as those in the examples above typically show activities in the low micromolar range for *Plasmodium falciparum* enzyme ($K_I$) and cell culture ($ED_{50}$), with selectivity (SI) over the human enzyme of at least 10-fold:

| R | Ki uM | SI | ED₅₀ uM |
|---|---|---|---|
| Ph₃CO | 1.8 | 10 | 6 |
| TBDPSO | 4.2 | 191 | 6.6 |
| TPSO | 2.8 | 324 | 1.1 |
| Ph₃CNH | 0.2 | 230 | 4.5 |
| Ph₃CO | 515 | nd | 1 |
| Ph₃NH | 313 | nd | 1.8 |
| TBDPSO | 1.2 | >833 | 3.0 |
| TPSO | 1.3 | >769 | 1.0 |
| TBDPSO | 89 | 9 | 8.8 |
| TPSO | 975 | nd | 1.0 |
| Ph₃CO | 5 | 91 | 2.0 |
| Ph₃NH | 12 | >83 | 5.3 |

Abbreviations

| | | | |
|---|---|---|---|
| TBDPSO | tert-butyldiphenylsilyloxy | DMF | dimethylformamide |
| TPSO | triphenylsilyloxy | DCM | dichloromethane |
| TBDMS | tert-butyldimethylsilyl | RT | room temperature |
| THF | tetrahydrofuran | Ac | acetyl |
| TEA | triethylamine | LAH | lithiumaluminiumhydride |
| TLC | thin layer chromatography | DMAP | dimethylaminopyridine |

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The invention claimed is:

1. A method of treatment of plasmodium infections in mammals, including man, comprising administering to an individual in need thereof an effective amount of formula I

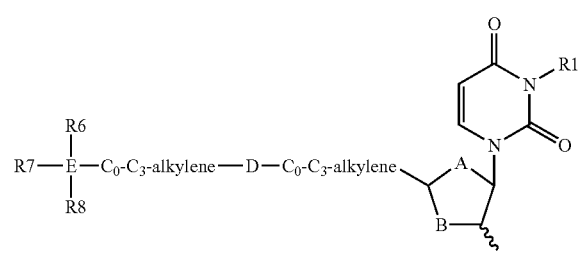

where
A is O, S or $CH_2$;
B is O, S or $CHR^3$;
$R^1$ is H, $C_1$-$C_5$ alkyl, $C_2$-$C_5$ alkenyl, $C_2$-$C_5$ alkynyl or a 5 or 6 membered, saturated or unsaturated ring containing 0 to 3 heteroatoms selected from N, O and S, the alkyl, alkenyl, alkynyl or ring being independently optionally substituted with $R^4$;
$R^2$ is H, F;
$R^3$ is H, F, OH, $NH_2$ or a pharmaceutically acceptable ester, amide or ether thereof; or
$R^2$ and $R^3$ together form a chemical bond;
D is —NHCO—, —CONH—, —O—, —C(=O)—, —CH=CH, —C≡C—, —$NR^5$—;
$R^4$ is independently selected from hydrogen, halo, cyano, amino, nitro, carboxy, carbamoyl, hydroxy, oxo, $C_1$-$C_5$ alkyl, $C_1$-$C_5$ haloalkyl, $C_1$-$C_5$ alkyloxy, $C_1$-$C_5$ alkanoyl, $C_1$-$C_5$ alkanoyloxy, $C_1$-$C_5$ alkylthio, —N($C_0$-$C_3$-alkyl)$_2$, hydroxymethyl, aminomethyl, carboxymethyl; —$SO_n$N($C_0$-$C_3$-alkyl), —$SO_n$$C_1$-$C_5$-alkyl, where n is 1 or 2;
$R^5$ is H, $C_1$-$C_4$ alkyl, $C_1$-$C_4$ alkanoyl;
E is Si or C;
$R^6$, $R^7$ and $R^8$ are independently selected from $C_1$-$C_8$ alkyl, $C_2$-$C_8$ alkenyl, $C_2$-$C_8$ alkynyl, or a stable monocyclic, bicyclic or tricyclic ring system which is saturated or unsaturated in which each ring has 0 to 3 heteroatoms selected from N, O and S;
$R^6$, $R^7$ and $R^8$ are independently optionally substituted with $R^4$;
with the proviso that if $R^3$ is H, OH, F, $NH_2$ or a bond, then at least one of $R^6$, $R^7$ and/or $R^8$ comprises an unsaturated ring;
or a pharmaceutically acceptable salts thereof.

2. The method according to claim 1, wherein A is —O— and B is —$CHR^3$—, or A is —O— and B is —S—.

3. The method according to claim 1, wherein $R^2$ and $R^3$ form a chemical bond.

4. The method according to claim 1, wherein $R^3$ is OH, $NH_2$ or F.

5. The method according to claim 1, wherein $R^1$ is H.

6. The method according to claim 1, wherein $C_0$-$C_3$-alkylene-D-$C_0$-$C_3$-alkylene is oxymethylene, oxyethylene or oxypropylene.

7. The method according to claim 1, wherein $C_0$-$C_3$-alkylene-D-$C_0$-$C_3$-alkylene is aminomethylene, aminoethylene or aminopropylene.

8. The method according to claim 1, wherein at least two of $R^6$, $R^7$ and $R^8$ have an aromatic nature.

9. The method according to claim 1, wherein $R^6$ is optionally substituted phenyl.

10. The method according to claim 9, wherein $R^8$ is optionally substituted phenyl or pyridyl.

11. The method according to claim 1, wherein E is C.

12. A compound of the formula I

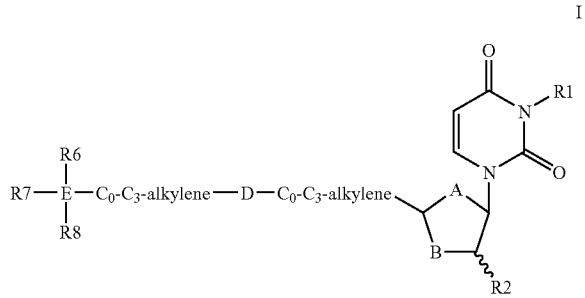

where

A is O, S or $CH_2$;

B is O, S or $CHR^3$;

$R^1$ is H, $C_1$-$C_5$ alkyl, $C_2$-$C_5$ alkenyl, $C_2$-$C_5$ alkynyl or a 5 or 6 membered, saturated or unsaturated ring containing 0 to 3 heteroatoms selected from N, O and S, the alkyl, alkenyl, alkynyl or ring being independently optionally substituted with $R^4$;

$R^2$ is H, F;

$R^3$ is H, F, OH, $NH_2$ or a pharmaceutically acceptable ester, amide or ether thereof or $R^2$ and $R^3$ together form a chemical bond;

D is —NHCO—, —CONH—, —O—, —C(=O)—, —CH=CH, —C≡C—, —$NR^5$—;

$R^4$ is independently selected from hydrogen, halo, cyano, amino, intro, carboxy, carbamoyl, hydroxy, oxo, $C_1$-$C_5$ alkyl, $C_1$-$C_5$ haloalkyl, $C_1$-$C_5$ alkyloxy, $C_1$-$C_5$ alkanoyl, $C_1$-$C_5$ alkanoyloxy, $C_1$-$C_5$ alkylthio, —N($C_0$-$C_3$-alkyl)$_2$, hydroxymethyl, aminomethyl, carboxymethyl; —$SO_n$N($C_0$-$C_3$-alkyl), —$SO_n C_1$-$C_5$-alkyl, where n is 1 or 2;

$R^5$ is H, $C_1$-$C_4$-allyl, $C_1$-$C_4$-alkanoyl;

E is Si or C;

$R^6$ and $R^7$ are independently a stable monocyclic, bicyclic or tricyclic ring system which has an aromatic nature and wherein each ring has 0 to 3 heteroatoms selected from N, O and S;

$R^8$ is $C_1$-$C_8$ alkyl, $C_2$-$C_8$ alkenyl, $C_2$-$C_8$ alkynyl, or a stable monocyclic, bicyclic or tricyclic ring system which is saturated or unsaturated and in which each ring has 0 to 3 heteroatoms selected from N, O and S;

$R^6$, $R^7$ and $R^8$ are independently optionally substituted with $R^4$;

with the proviso that if the group $C_0$-$C_3$alkyl-D-$C_0$-$C_3$ alkyl is —O—$CH_2$—, then the group E(R6)(R7)(R8) is not $CPh_3$ (trityl), methoxylated trityl or tert.butyldiphenylsilyl;

and pharmaceutically acceptable salts thereof.

13. A compound according to claim 12, wherein A is —O— and B is —$CHR^3$—, or A is —O and B is —S—.

14. A compound according to claim 12, wherein $R^2$ and $R^3$ form a chemical bond.

15. A compound according to claim 12, wherein $R^3$ is OH, $NH_2$ or F.

16. A compound according to claim 12, wherein $R^1$ is H.

17. A compound according to claim 12, wherein $C_0$-$C_3$-alkylene-D-$C_0$-$C_3$-alkylene is oxymethylene, oxyethylene or oxypropylene.

18. A compound according to claim 12, wherein $C_0$-$C_3$-alkylene-D-$C_0$-$C_3$-alkylene is aminomethylene, aminoethylene or aminopropylene.

19. A compound according to claim 12, wherein $R^6$ is optionally substituted phenyl.

20. A compound according to claim 19 wherein $R^7$ is optionally substituted phenyl or pyridyl.

21. A compound according to claim 12 wherein E is C.

22. A pharmaceutical composition comprising a compound as defined in claim 12 and a pharmaceutically acceptable carrier or diluent therefor.

* * * * *